United States Patent
Wang

(10) Patent No.: US 9,299,146 B2
(45) Date of Patent: Mar. 29, 2016

(54) IMAGE PROCESSING DEVICE, IMAGE PROCESSING METHOD AND IMAGE PROCESSING PROGRAM

(71) Applicant: FUJIFILM Corporation, Tokyo (JP)

(72) Inventor: Caihua Wang, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 86 days.

(21) Appl. No.: 14/307,405

(22) Filed: Jun. 17, 2014

(65) Prior Publication Data

US 2014/0294274 A1 Oct. 2, 2014

Related U.S. Application Data

(63) Continuation of application No. PCT/JP2012/007907, filed on Dec. 11, 2012.

(30) Foreign Application Priority Data

Dec. 20, 2011 (JP) .................................. 2011-278238
Nov. 6, 2012 (JP) .................................. 2012-244541

(51) Int. Cl.
*G06T 7/00* (2006.01)
*G01R 33/56* (2006.01)
(Continued)

(52) U.S. Cl.
CPC ............. *G06T 7/0014* (2013.01); *G06T 7/0026* (2013.01); *G06T 7/0034* (2013.01); *A61B 6/5229* (2013.01); *A61B 8/5238* (2013.01); *G01R 33/5608* (2013.01); *G06T 2207/10081* (2013.01);
(Continued)

(58) Field of Classification Search
CPC ... G06T 7/0014; G06T 7/0024; G06T 7/0026; G06T 7/0034; G06T 2007/10072; G06T 2207/10081; G06T 2207/10104; G06T 2207/200076; A61B 6/5229; A61B 6/5235; A61B 6/5247; A61B 8/5238; A61B 8/5261
See application file for complete search history.

(56) References Cited

U.S. PATENT DOCUMENTS

2006/0029291 A1* 2/2006 Sun et al. ...................... 382/294

FOREIGN PATENT DOCUMENTS

JP 2008-142137 A 6/2008

OTHER PUBLICATIONS

International Search Report (ISR) (PCT Form PCT/ISA/210), in PCT/JP2012/007907, dated Feb. 12, 2013.
(Continued)

*Primary Examiner* — Andrew W Johns
(74) *Attorney, Agent, or Firm* — McGinn IP Law Group, PLLC

(57) ABSTRACT

A first image and a second image obtained by imaging the same subject with different types of modalities are obtained. The first image is deformed, and similarity between the deformed first image and the second image is evaluated by an evaluation function that evaluates correlation between distributions of corresponding pixel values of the two images to estimate an image deformation amount of the first image. Based on the estimated image deformation amount, a deformed image of the first image is generated. The evaluation function includes a term representing a measure of correlation between a pixel value of the deformed first image and a corresponding pixel value of the second image, wherein the term evaluates the correlation based on probability information that indicates a probability of each combination of corresponding pixel values of the first image and the second image.

13 Claims, 6 Drawing Sheets

(51) Int. Cl.
A61B 6/00 (2006.01)
A61B 8/08 (2006.01)
(52) U.S. Cl.
CPC ............... G06T 2207/10104 (2013.01); G06T 2207/20076 (2013.01); G06T 2207/30016 (2013.01)

(56) References Cited

OTHER PUBLICATIONS

D. Mattes et al., "Nonrigid multimodality image registration", Proceedings of the SPIE, vol. 4322, pp. 1609-1620, 2001.

C.L. Lin and Y.W. Chen, "PCA Based Regional Mutual Information for Robust Medical Image Registration", IEICE Technical Report, vol. 109, No. 65, pp. 23-28, 2009.

J. Tsao, "Multimodality Image Registration by Gradient Enhanced Generalized Clustering", Proc. Intl. Soc. Mag. Reson. Med. 7, No. 125, 1999.

J.W. Jeone et al., "Multi-modal MR Image Registration Using Mutual Information and Simulated Annealing", Proc. Intl. Soc. Mag. Reson. Med. 10, No. 2480, 2002.

Extended European Search Report dated Oct. 13, 2015.

Masashi Sugiyama et al: "Information-Maximization Clustering Based on Squared-Loss Mutual Information", arxiv.org, Cornell University Library, 201 Olin Library Cornell University Ithaca, NY 14853, Dec. 3, 2011, XP080554851.

Thevenaz P. et al: "An Efficient Mutual Information Optimizer for Multiresolution Image Registration", Image Processing, 1998. ICIP 98. Proceedings. 1998 International Conference on Chicago, IL, USA Oct. 4-7, 1998, Los Alamitos, CA, USA, IEEE Comput. Soc, US, vol. 1, Oct. 4, 1998, pp. 833-837, XP010308885.

* cited by examiner

V1

V2

V1A

V2

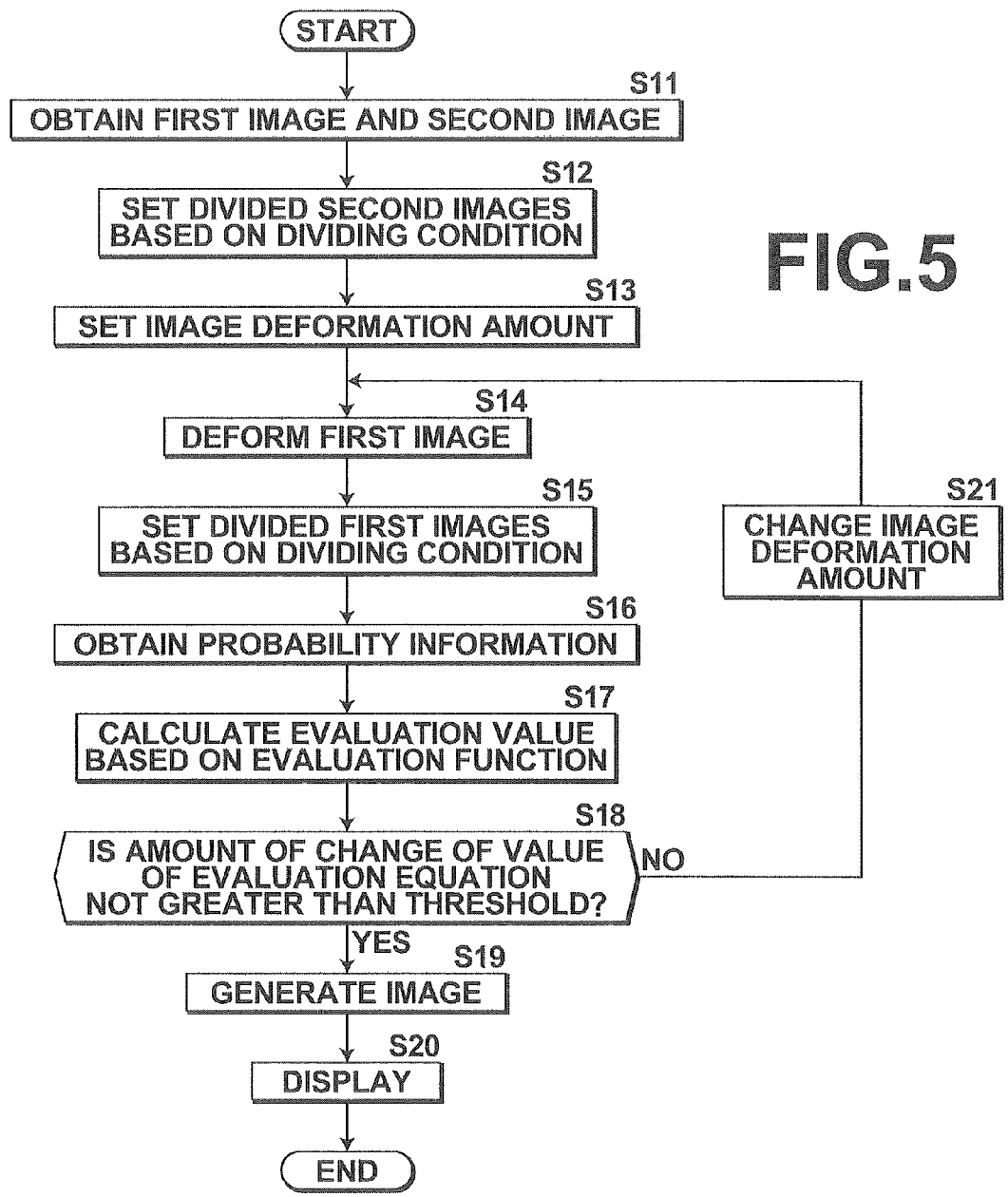

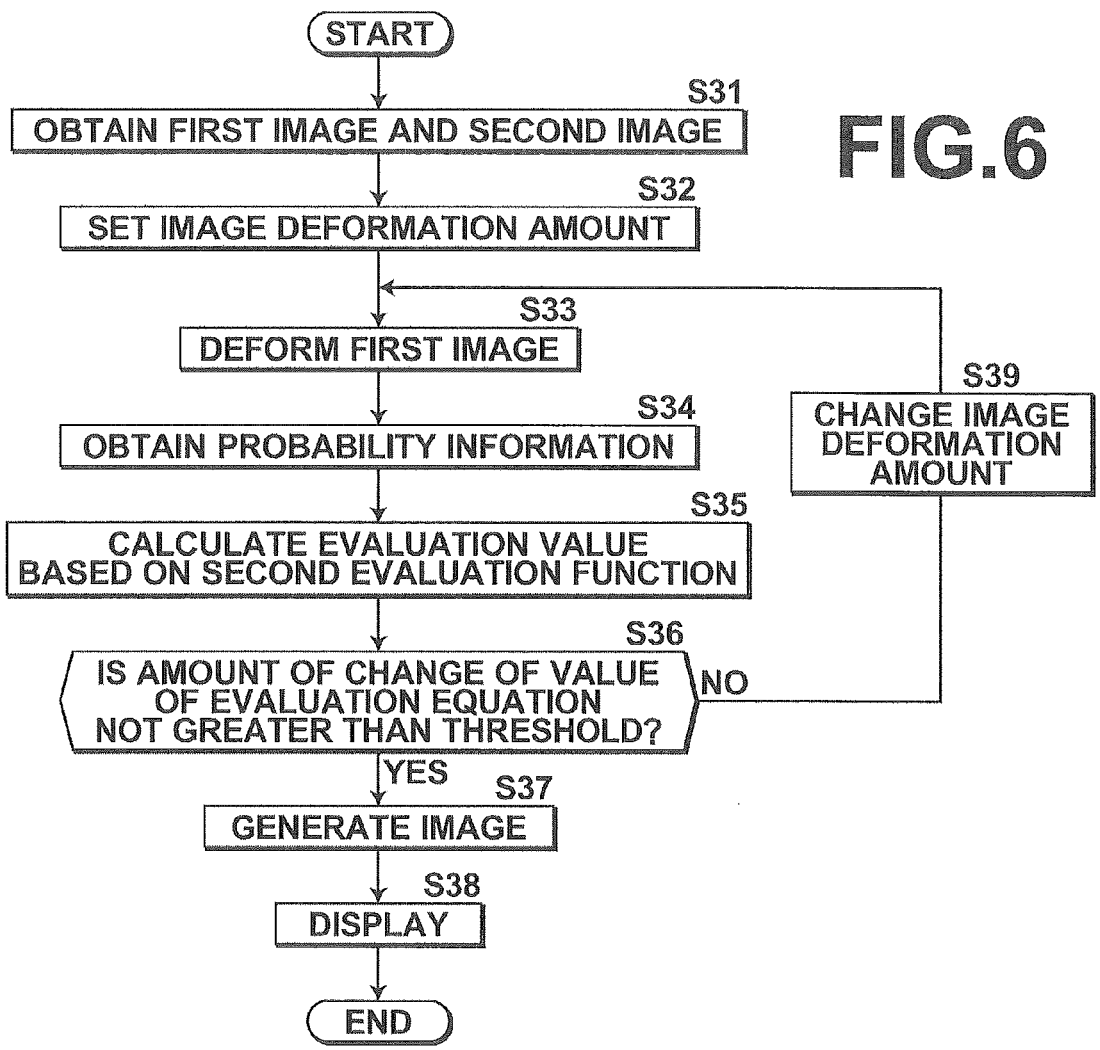

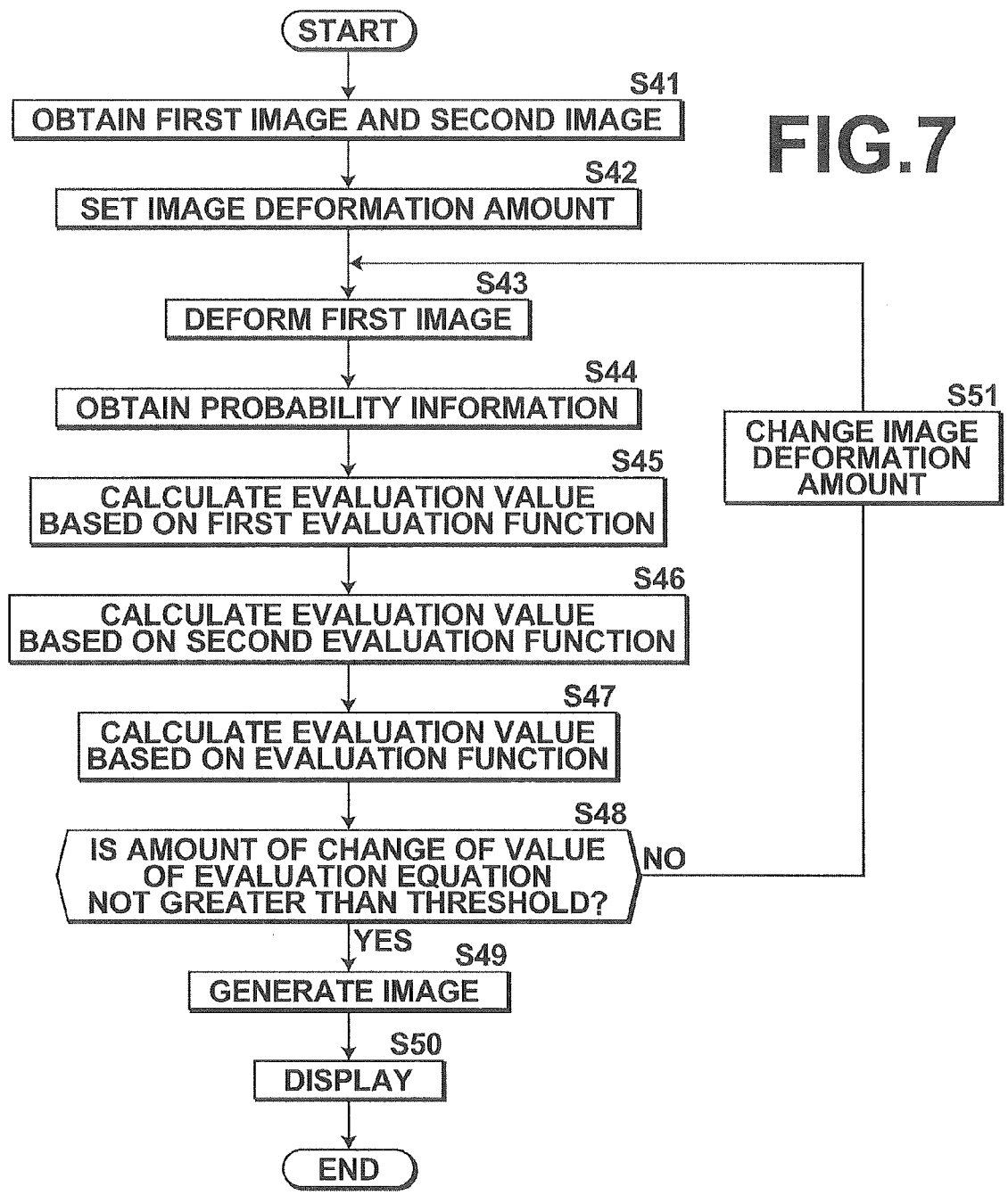

IMAGE PROCESSING DEVICE, IMAGE PROCESSING METHOD AND IMAGE PROCESSING PROGRAM

CROSS-REFERENCE TO RELATED APPLICATIONS

This application is a Continuation of PCT International Application No. PCT/JP2012/007907 filed on Dec. 11, 2012, which claims priority under 35 U.S.C. §119 (a) to Japanese Patent Application No. 2011-278238 filed on Dec. 20, 2011 and Japanese Patent Application No 2012-244541 filed on Nov. 6, 2012. Each of the above applications is hereby expressly incorporated by reference, in its entirety, into the present application.

TECHNICAL FIELD

The present invention relates to an image processing device, an image processing method and an image processing program for generating, for two images that are obtained by imaging the same subject, a deformed image of one of the two images by deforming the image space of the one of the images to make the spatial positions of the subject in the two images conform to each other.

BACKGROUND ART

In diagnostic imaging using two three-dimensional images that are obtained by imaging the same subject at different times with the same or different imaging apparatuses (modalities), a non-rigid registration technique is attracting attention, where a transformation function that makes the spatial positions of the subject in the two images conform to each other when the images are superposed one on the other is estimated, and one of the images is deformed using the estimated transformation function, thereby registering the two images. In the non-rigid registration technique, control points that divide the image space at given intervals are set, and an image deformation amount of each control point that maximizes an evaluation function, which evaluates similarity between pixel values of the one of the images deformed by displacing the control points and the other of the images, is determined. Then, based on the image deformation amount of each control point, a transformation function is estimated.

D. Mattes et al., "Nonrigid multimodality image registration", Proceedings of the SPIE, vol. 4322, pp. 1609-1620, 2001 (hereinafter, Non-Patent Document 1) teaches applying the non-rigid registration to images that are obtained by imaging the same subject with different types of modalities, a PET (Positron Emission Tomography) apparatus and a CT (Computed Tomography) apparatus, where an amount of mutual information is used in the evaluation function as a measure of similarity between pixel values of the two types of images.

DISCLOSURE OF INVENTION

With respect to two images obtained by imaging the same subject with different types of modalities, pixel values of one of the images corresponding to pixel values of the other of the images belong to a somewhat limited range depending on the types of modalities and the types of imaging methods of the modalities. However, with the technique taught in Non-Patent Document 1 where only the correlation between distributions of pixel values of the two images is used as the measure of similarity between the two images, there may be a case where, for example, a high degree of similarity is calculated for an actually impossible combination of a pixel value of the deformed one of the images and a pixel value of the other of the images. If the similarity is evaluated incorrectly and transformation parameters to deform the one of the images are determined based on the incorrect evaluation, registration between the deformed one of the images and the other of the images may not be achieved. Therefore, it is desired to more accurately evaluate the similarity by discriminating whether or not each combination of pixel values of the two images is reasonable.

In view of the above-described circumstances, the present invention is directed to providing an image processing device, an image processing method and an image processing program that allow, for two images obtained by imaging the same subject with different types of modalities, achieving more correct evaluation of the similarity between the two images with reflecting a probability of each combination of pixel values on the evaluation of the similarity, thereby allowing accurate estimation of an image deformation amount to deform one of the images to make the positions of the subject in the two images conform to each other.

In order to accomplish the above-described object, the image processing device according to the invention comprises: an image obtaining unit for obtaining a first image obtained by imaging a subject with a first modality and a second image obtained by imaging the subject with a second modality, the second modality being different from the modality with which the first image is obtained; an image deformation amount estimation unit for estimating an image deformation amount for deforming the first image to provide a deformed first image that is similar to the second image by deforming the first image and evaluating similarity between the deformed first image and the second image with an evaluation function, the evaluation function evaluating correlation between distributions of pixel values of the deformed first image and corresponding pixel values of the second image; and an image generation unit for generating a deformed image of the first image based on the estimated image deformation amount, wherein the image deformation amount estimation unit comprises a probability information obtaining unit for obtaining probability information indicating a probability of each combination of corresponding pixel values of the first image and the second image, and the evaluation function includes a term representing a measure of correlation between a pixel value of the deformed first image and a corresponding pixel value of the second image, wherein the term evaluates the correlation based on the obtained probability information.

The image processing method according to the invention is an image processing method executed on the image processing device, the method comprising the steps of: obtaining a first image obtained by imaging a subject with a first modality and a second image obtained by imaging the subject with a second modality, the second modality being different from the modality with which the first image is obtained; estimating an image deformation amount for deforming the first image to provide a deformed first image that is similar to the second image by deforming the first image and evaluating similarity between the deformed first image and the second image with an evaluation function, the evaluation function evaluating correlation between distributions of pixel values of the deformed first image and corresponding pixel values of the second image; and generating a deformed image of the first image based on the estimated image deformation amount, wherein the step of estimating the image deformation amount comprises the step of obtaining probability information indicating a probability of each combination of corresponding pixel values of the first image and the second image, and the evaluation function includes a term representing a measure of correlation between a pixel value of the deformed first image and a corresponding pixel value of the second image, wherein the term evaluates the correlation based on the obtained probability information.

The image processing program of the invention causes a computer to execute the above-described method.

The first image and the second image in the invention are images showing the same subject imaged at different times with different modalities, and examples of modalities applicable to the first or second modality in the invention include CT, MRI, PET, SPECT and ultrasound images.

To "the evaluation function including a term representing a measure of correlation between a pixel value of the deformed first image and a corresponding pixel value of the second image, wherein the term evaluating the correlation based on the obtained probability information" in the invention, any of various evaluation methods that evaluates the similarity as low similarity when the probability of each combination of corresponding pixel values of the deformed first image and the second image is determined to be low based on the probability information is applicable.

For example, in a first aspect of the image processing device according to the invention, it is preferable that the term representing a measure of correlation in the evaluation function be weighted with the probability information.

In the first aspect of the image processing device according to the invention, the probability information may be any information that indicates a probability of each combination of pixel values of the first image and the second image. For example, the probability information may indicate a conditional probability of occurrence of an event where each pixel value the first image is obtained, given an event where each pixel value of the second image is obtained.

In the first aspect of the image processing device according to the invention, the evaluation function may be any evaluation function that includes a term representing a measure of correlation between a pixel value of the deformed first image and a pixel value of the second image, wherein the similarity between the deformed first image and the second image is calculated based on the term representing a measure of correlation weighted based on the probability information. For example, the evaluation function may be defined such that a greater evaluation value is calculated when the similarity between the two images is higher, or a smaller evaluation value is calculated when the similarity between the two images is higher. It should be noted that, in the case where the evaluation function is defined such that a greater evaluation value is calculated when the similarity between the two images is higher, the probability information is weighted such that a greater evaluation value is calculated for a combination of pixel values of the two images with a higher probability. On the other hand, in the case where the evaluation function is defined such that a smaller evaluation value is calculated when the similarity between the two images is higher, the probability information is weighted such that a smaller evaluation value is calculated for a combination of pixel values of the two images with a higher probability.

In the first aspect of the image processing device according to the invention, it is preferable that the term representing a measure of correlation in the evaluation function represent an amount of mutual information or an amount of square loss mutual information with a pixel value of the deformed first image and a pixel value of the second image being discrete probability variables.

In the first aspect of the image processing device according to the invention, it is preferable that the probability information indicate a conditional probability of occurrence of an event where each pixel value of a first reference image obtained by imaging an additional subject with the first modality is obtained, given an event where each pixel value of a second reference image obtained by imaging the additional subject with the second modality is obtained. In this case, it is preferable that the additional subject be another subject of the same type as the subject shown in the first and second images.

In the first aspect of the image processing device according to the invention, it is preferable that the probability information be further weighted with a reciprocal of a probability density function obtained by approximating a pixel value distribution of the first reference image to a uniform distribution in order to adjust the weighting with the conditional probability.

In the first aspect of the image processing device according to the invention, the probability information may associate, for each type of subject, a first range of pixel values obtained by imaging a given type of subject with the first modality with a second range of pixel values obtained by imaging the given type of subject with the second modality, and the evaluation function may be weighted based on the probability information such that, if pixel values of the deformed first image and the second image do not satisfy the first range of pixel values and the second range of pixel values associated with the first range of pixel values, the similarity between the deformed first image and the second image is evaluated as low similarity.

In this case, it is preferable that the first and second ranges of pixel values be calculated by estimating, for each type of subject, the first and second ranges of pixel values based on imaging principles of the first and second modalities.

It should be noted that the "type of subject" may be set arbitrarily as long as it represents an identifiable subject in diagnostic images. For example, subjects can be classified into types based on a composition, an anatomic structure, an element forming an anatomic structure, a histology of an anatomic structure, etc., each showing a certain range of pixel values. As one example, water, air and each anatomic structure can be defined as different types.

In a second aspect of the image processing device according to the invention, it is preferable that the probability information represent a conditional probability of occurrence of an event where each pixel value of a first reference image obtained by imaging an additional subject with the first modality is obtained, given an event where each pixel value of a second reference image obtained by imaging the additional subject with the second modality is obtained, and the term representing a measure of correlation in the evaluation function represent a difference between the probability information and a joint probability distribution with a pixel value of the deformed first image and a pixel value of the second image being discrete probability variables.

In the second aspect of the image processing device according to the invention, it is preferable that an evaluation function defined by Equation (9) below be used as the evaluation function:

$$S_D(\mu) = -\sum_{f \in F}\sum_{m \in M} p(f, m; \mu)\log\frac{p(f, m; \mu)}{p_L(m; \mu \mid f)p(f)} \quad (9)$$

where f is a pixel value of the second image, m is a pixel value of the first image, F is a set of all pixel values of the second image, M is a set of all pixel values of the first image, $m;\mu$ is a pixel value of the deformed first image when the deformation amount of the first image is $\mu$, $p(f, m;\mu)$ is a joint probability distribution with the pixel value of the deformed first image and the pixel value of the second image being discrete probability variables, $p(f)$ is a marginal probability distribution with the pixel value of the second image being a discrete probability variable, and $P_L(m;\mu|f)$ is the probability information.

It is preferable that the evaluation function in the second aspect of the invention include an additional evaluation function for evaluating correlation between distributions of pixel values of the deformed first image and corresponding pixel values of the second image to evaluate the similarity between the deformed first image obtained by deforming the first image and the second image, and the additional evaluation function include a term representing a measure of correlation between a pixel value of the deformed first image and a corresponding pixel value of the second image, wherein the term represents an amount of mutual information or an amount of square loss mutual information with the pixel value of the deformed first image and the pixel value of the second image being discrete probability variables.

In the second aspect of the image processing device according to the invention, the term representing a measure of correlation between a pixel value of the deformed first image and a corresponding pixel value of the second image in the additional evaluation function may be weighted based on the obtained probability information.

It should be noted that "high" with respect to the similarity as used herein refers to that the deformed first image and the second image are similar to each other and "low" with respect to the similarity as used herein refers to that the images are not similar to each other. The description "weighted such that the similarity is evaluated as low similarity" herein means that being weighted such that a smaller similarity value is calculated when the evaluation function is defined such that a greater evaluation value is calculated when the similarity between the two images is higher, or being weighted such that a greater similarity value is calculated when the evaluation function is defined such that a smaller evaluation value is calculated when the similarity between the two images is higher.

According to the invention, the image obtaining unit for obtaining a first image obtained by imaging a subject with a first modality and a second image obtained by imaging the subject with a second modality, the second modality being different from the modality with which the first image is obtained; the image deformation amount estimation unit for estimating an image deformation amount for deforming the first image to provide a deformed first image that is similar to the second image by deforming the first image and evaluating similarity between the deformed first image and the second image with an evaluation function, the evaluation function evaluating correlation between distributions of pixel values of the deformed first image and corresponding pixel values of the second image; and the image generation unit for generating a deformed image of the first image based on the estimated image deformation amount are provided, wherein the image deformation amount estimation unit comprises a probability information obtaining unit for obtaining probability information indicating a probability of each combination of corresponding pixel values of the first image and the second image, and the evaluation function includes a term representing a measure of correlation between a pixel value of the deformed first image and a corresponding pixel value of the second image, wherein the term evaluates the correlation based on the obtained probability information. This allows evaluating the similarity as low similarity for an actually impossible combination of pixel values depending on the probability information, thereby allowing more accurate evaluation of the similarity than that with the conventional technique, and an image of the first image that is registered to the second image can preferably be generated as a result.

BRIEF DESCRIPTION OF THE DRAWINGS

FIG. 5 is a flow chart illustrating operation of the image processing device according to the fourth embodiment of the invention, FIG. 6 is a flow chart illustrating operation of the image processing device according to a second embodiment of the invention, and FIG. 7 is a flow chart illustrating operation of the image processing device according to a third embodiment of the invention.

DESCRIPTION OF PREFERRED EMBODIMENTS

Hereinafter, embodiments of an image processing device, an image processing program and an image processing method of the present invention will be described in detail with reference to the drawings. The invention is applicable to various fields where two images obtained by imaging the same subject at different times with different modalities are registered to each other. For the purpose of illustration, the invention is described herein based on an example where the invention is applied to diagnostic imaging in the medical field.

Figure 1:
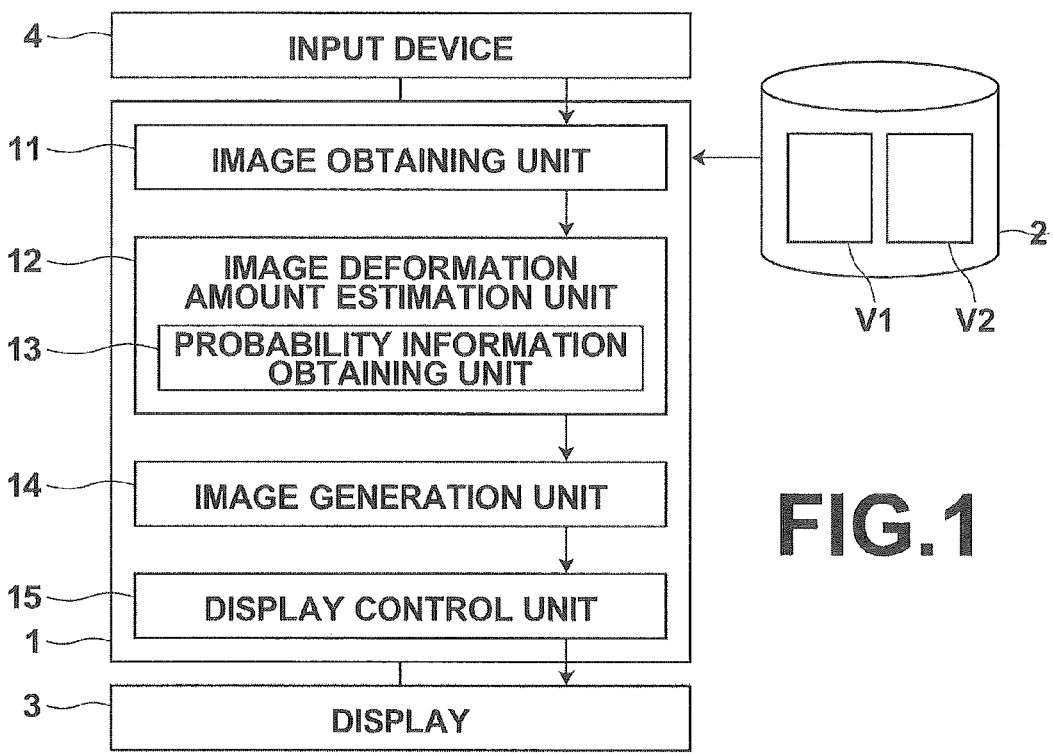
FIG. 1 is an electrical schematic block diagram of an image processing device according to a first embodiment of the invention.

FIG. 1 illustrates the schematic configuration of the image processing device that is implemented by installing the image processing program on a workstation used by doctors. The image processing device 1 includes, as a standard configuration of a workstation, a processor and a memory (which are not shown in the drawing), and also includes a storage 2, such as a HDD (Hard Disk Drive). To the image processing device 1, a display 3 and an input device 4, such as a mouse, a keyboard, etc., is connected.

The image processing program and data referenced by the image processing program are stored in the storage 2 at the time of install and is loaded in a memory at the time of start-up. The image processing program prescribes, as processes executed by the CPU, an image obtaining process, an image deformation amount estimating process, an image generation process and a display control process.

Then, when the CPU executes these processes according to the prescription of the program, the general-purpose workstation functions as an image obtaining unit 11, an image deformation amount estimation unit 12, an image generation unit 14 and a display control unit 15, which will be described later.

Figure 3A:
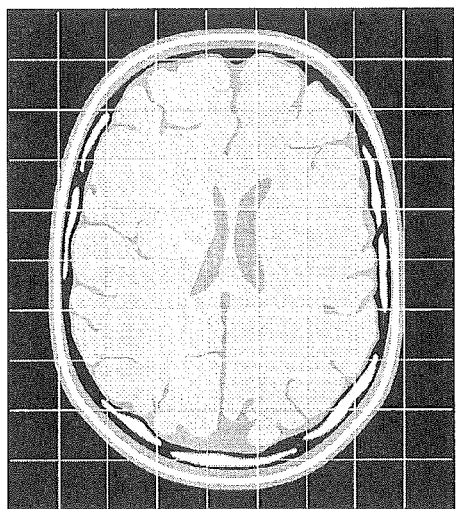
FIG. 3A shows one example of a first image (MR image) and a second image (CT image) before registration.
Figure 3A:
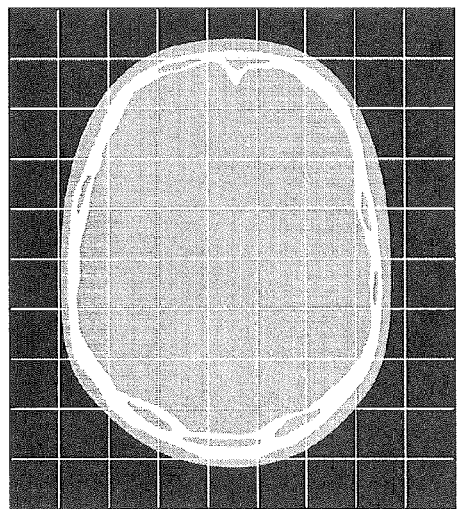

In the storage 2, a first image and a second image transferred from an examination department in charge of imaging or a first image and a second image obtained by searching a database are stored. In this embodiment, a first image V1 (MR image) and a second image V2 (CT image), which are obtained during examination of a given patient by imaging the head of the patient with different modalities on the same day at different times, are transferred from the examination department, an operation to unify scales of the two images V1 and V2 into the scale of one of the two images V1 and V2 is performed based on a pixel spacing and a slice spacing obtained from information, such as header information, of the two images V1 and V2 by a known method, and the images are stored in the storage 2. FIG. 3A shows example images of the first image V1 and the second image V2. Comparing the first image V1 with the second image V2, the anatomic structures, such as the skull, in the first image are larger than the corresponding anatomic structures in the second image, and characteristic positions of the anatomic structures, such as positions of the boundary between the right and left cerebral hemispheres, in the first and second images are not the same.

The image obtaining unit 11 obtains the first image V1 and the second image V2 from the storage 2 and loads the images in the memory. In this embodiment, when the image processing device 1 detects that a predetermined registration function is selected from a selection menu, the image processing device 1 prompts the user to select or input information that is necessary to identify the first and second images. As the first and second images are identified by operation by the user via the input device 4, the image obtaining unit 11 obtains the first image V1 and the second image V2 from the storage 2 and loads the images in the memory.

The image deformation amount estimation unit 12 deforms the first image V1, and evaluates similarity between a deformed first image V1a and the second image V2 with an evaluation function $S(\mu)$, which evaluates correlation between distributions of pixel values of the deformed first image V1a and corresponding pixel values of the second image V2, to estimate an image deformation amount of the first image that makes the positions of the subject in the deformed first image and in the second image conform to each other.

More particularly, the image deformation amount estimation unit 12 sets a set X of control points x1, x2, . . . and xn that divide the image space at given intervals on each of the deformed first image V1a and the second image V2. Hereinafter, the set of the control points x1, x2, . . . and xn is referred to as "control points X". It should be noted that the image deformation amount estimation unit 12 deforms the first image V1 by displacing each control point X of the first image V1 by an image deformation amount $\mu$ according to a transformation function g. Hereinafter, a resulting control point after each control point X of the first image V1 is displaced by the image deformation amount $\mu$ according to the transformation function g is referred to as "control point $g(X,\mu)$", and a resulting image after the first image V1 is deformed by displacing each control point X of the first image V1 by the image deformation amount $\mu$ according to the transformation function g is referred to as "deformed first image V1a". It should be noted that the image deformation amount estimation unit 12 of this embodiment sets the control points X and the image deformation amount $\mu$ according to the method disclosed in Non-Patent Document 1 and uses the transformation function g disclosed in Non-Patent Document 1 as the transformation function g.

Subsequently, the image deformation amount estimation unit 12 obtains a pixel value $M(g(X,\mu))$ at each control point $g(X,\mu)$ of the deformed first image V1a and obtains a pixel value $F(X)$ at each control point X of the second image V2. Then, the image deformation amount estimation unit 12 determines the image deformation amount $\mu$ of each control point X that maximizes the evaluation function $S(\mu)$ (registration function) for evaluating similarity between a pixel value $M(g(X,\mu))$ at each control point $g(X,\mu)$ of the deformed first image V1a and a pixel value $F(X)$ at each control point X of the second image V2, and estimates a transformation function for the first image V1 based on the determined image deformation amount $\mu$ of each control point X.

In this first embodiment, the image deformation amount estimation unit 12 evaluates the similarity between the deformed first image V1a and the second image V2 using the evaluation function $S(\mu)$, which is expressed by Equation (3) described later. According to the evaluation function $S(\mu)$ in this embodiment, the higher the similarity between distributions of pixel values of the deformed first image V1a and the second image V2, the greater the value of the evaluation function $S(\mu)$. Therefore, the image deformation amount estimation unit 12 determines, with changing the image deformation amount $\mu$, an image deformation amount $\mu$ that makes an amount of change of the evaluation function $S(\mu)$ (or an absolute value of a partial derivative $\nabla S(\mu)$ with respect to $\mu$) be not greater than a predetermined threshold value as an image deformation amount that achieves the maximum value of the similarity between the two images (an image deformation amount that achieves the highest similarity between the two images). Then, the image deformation amount estimation unit 12 determines the transformation function for deforming the first image V1 based on the determined image deformation amount $\mu$. It should be noted that the predetermined threshold value may be set to any value that is regarded as a sufficiently small value of the amount of change of the evaluation function $S(\mu)$ expressed by Equation (3). Further, any of various known methods can be applied to the determination of the transformation function for deforming the first image V1 based on the image deformation amount $\mu$. In this example, the method disclosed in Non-Patent Document 1 is applied.

It should be noted that, although the evaluation function is defined such that a greater value of the similarity (evaluation value) indicates higher similarity in this example, the evaluation function may be defined such that a smaller evaluation value indicates higher similarity. Further, the image deformation amount $\mu$ that achieves the maximum similarity value may be identified using any method for calculating the maximum value (or the minimum value) of an evaluation function according to the non-rigid registration technique, as long as the method can identify the image deformation amount that achieves the maximum (or minimum) evaluation value (similarity) of the evaluation function. Further, an evaluation value according to the evaluation function $S(\mu)$ may be calculated for each of different image deformation amounts $\mu$, and the maximum (or minimum) evaluation value among the calculated evaluation values may be identified to identify the image deformation amount $\mu$ that corresponds to the identified maximum evaluation value (or minimum evaluation value).

The image deformation amount estimation unit 12 of this first embodiment includes a probability information obtaining unit 13, which obtains, as probability information, a probability of each combination of corresponding pixel values of the first image and the second image, and a term representing a measure of similarity in the evaluation function is weighted based on the probability information.

Now, a conventional evaluation function is described first, and then the evaluation function and the probability information of the first embodiment is described in detail.

As shown in Non-Patent Document 1, in the non-rigid registration technique for registering a first image and a second image that are obtained by imaging the same subject with different modalities, the similarity between a distribution of pixel values of the first image and a distribution of corresponding pixel values of the second image can be evaluated using an evaluation function based on an amount of mutual information.

The amount of mutual information represents a measure of correlation between two random variables f and m based on a joint probability distribution function p(f, m) of the two random variables f and m and marginal probability distribution functions p(f) and p(m) of the two random variables f and m. Typically, the amount of mutual information is defined by Equation (1) below:

$$I(f, m) = \sum_{f \in F} \sum_{m \in M} p(f, m) \log \frac{p(f, m)}{p(m)p(f)} \quad (1)$$

In Equation (1), f is a discrete probability variable belonging to a set F, and m is a discrete probability variable belonging to a set M. The higher the correlation between the two random variables f and m, the greater the amount of mutual information. In other words, if one of the variables can be estimated with a higher probability when the other variable is given, the amount of information is greater. It should be noted that the amount of mutual information is 0 when the two random variables are completely independent from each other.

With respect to images obtained by imaging the same subject with different modalities, the same type of subject in the images may have different pixel values (signal values) due to difference of the physical principle of imaging for obtaining the images. In this case, the similarity between the two images cannot be determined by simply comparing the pixel values. For example, a pixel value (a CT value) of a CT image is greater as a radiation absorption rate (a radiation transmittance) is higher, and pixel values of air, water, muscles and organ tissues, such as the liver or the heart, and bones increase in this order. On the other hand, a pixel value of a MR image is determined depending on nuclear magnetic resonance of hydrogen atoms contained in the object to be imaged, and the magnitude of a signal value of the object changes depending on the imaging method, such as a T1- or T2-weighted image. For example, in a T1-weighted MR image, pixel values of fat, muscles and water decrease in this order. Since the order of magnitude of pixel values of fat, muscles and water in a CT image is different from that in a T1-weighted MR image, the similarity between the two images cannot be determined by simply comparing the pixel values of these images.

Even in such a case, however, parts of the two images showing the same anatomic structure have distributions of pixel values in accordance with a common feature based on the same anatomic structure, and therefore there is a correlation between the distributions of pixel value of these images. Utilizing this fact, Non-Patent Document 1 teaches that the similarity between two images obtained by imaging the same subject with different modalities is determined such that the similarity is higher as the correlation between distributions of pixel values of the two images is higher, based on an amount of mutual information with pixel values of the two images being random variables. More specifically, an amount of mutual information with each pixel value m;μ of a deformed image of an image obtained with a first modality and each pixel value f of an image obtained with a second modality being the random variables is used as the evaluation function, as shown by Equation (2) below (hereinafter, each pixel value of the deformed image obtained by deforming the first image by the image deformation amount μ is designated as m;μ using the image deformation amount μ from the first image):

$$S(\mu) = -\sum_{f \in F} \sum_{m \in M} p(f, m; \mu) \log p \frac{(f, m; \mu)}{p(m; \mu)p(f)} \quad (2)$$

In Equation (2), the amount of mutual information indicates correlation between a distribution of the pixel values f of the second image and a distribution of the pixel values m;μ of the deformed first image and therefore functions as a measure of similarity between the second image and the deformed first image. It should be noted that the set F is a set of all the pixel values of the deformed first image, and the set M is a set of all the pixel values of the second image. Hereinafter, the evaluation function based on the amount of mutual information, such as one expressed by Equation (2), is referred to as the first evaluation function.

With the conventional evaluation function, as shown by Equation (2) above, however, probability of each combination of pixel values obtained depending on the type of each modality, etc., is not evaluated at all. Therefore, there is a problem (the first problem) that, even in a case where pixel values of the second image corresponding to pixel values of the deformed first image are expected to be within a somewhat limited range, this cannot be reflected on the evaluation of a calculated similarity value.

In view of this first problem, the present inventor has found that it is effective to introduce a term representing probability information, which indicates the probability of each combination of corresponding pixel values of the deformed first image and the second image, into the evaluation function. Then, as a first aspect thereof, probability information $P_L(m; \mu|f)$ is applied to the term representing a measure of similarity between the deformed first image and the second image in the evaluation function of Equation (2), as expressed by Equation (3) below:

$$S(\mu) = -\sum_{f \in F} \sum_{m \in M} p_L(m; \mu | f) p(f, m; \mu) \log \frac{p(f, m; \mu)}{p(m; \mu)p(f)} \quad (3)$$

That is, the term representing a measure of similarity between the deformed first image and the second image in the first evaluation function is weighted with the probability information $P_L(m;\mu|f)$ which indicates a probability of the combination of the two images depending on the probability of each combination of pixel values of the two images.

The probability information $P_L(m;\mu|f)$ may be any information as long as it defines a probability of each combination of corresponding pixel values of an image obtained by imaging a given subject with the first modality and an image obtained by imaging a given subject of the same type with the second modality. The "given subject" here may be the same as or different from the subject shown in the first image V1 and the second image V2.

In this embodiment, the probability of each combination of corresponding pixel values of the image obtained with the first modality and the image obtained with the second modality is defined as a conditional probability of occurrence of an event where, given an event where each pixel of the first image has a pixel value of f, each corresponding pixel of the second image has a pixel value of m;μ. It should be noted that a conditional probability distribution function can be calculated by a joint probability distribution function $p_L(f, m;μ)$ and a marginal probability distribution function $p_L(f)$ of the random variable f, as expressed by Equation (4) below:

$$p_L(m; μ \mid f) = \frac{p_L(f, m; μ)}{p_L(f)} \quad (4)$$

In this first embodiment, the probability information obtaining unit 13 obtains pixel values f(f∈F) at all control points of the deformed image obtained by deforming the first image by the image deformation amount μ, and pixel values m(m∈M) at corresponding control points of the second image. Then, using a known method, the probability information obtaining unit 13 obtains the joint probability distribution function $p_L(f, m;μ)$ by checking, for each pixel value f(f∈F) at the control points, a distribution of the pixel values m(m∈M) at the corresponding control points, and obtains the marginal probability distribution function $p_L(f)$ by checking a distribution of the pixel values f at the control points. Then, based on Equation (4), the probability information obtaining unit 13 obtains the probability information $P_L(m;μ|f)$.

It should be noted that, for the above-described calculation of the conditional probability, a first reference image obtained by imaging a given subject with the first modality and a second reference image obtained by imaging the same given subject with the second modality can be used. The given subject may not necessarily be the same type of subject as the subject shown in the first image and the second image; however, in order to achieve more accurate calculation of the probability information, it is preferred that the first reference image and the second reference image show the same type of subject as the subject shown in the first image and the second image. Further, there may be a pair of or pairs of first and second reference images. In a case where the conditional probability is calculated using pairs of first and second reference images, it is believed that more accurate estimation of the probability of each combination of pixel values can preferably be achieved.

The probability information $P_L(m;μ|f)$ may be calculated or obtained at any timing as long as it is performed before the calculation of the image deformation amount that maximizes the evaluation function S(μ).

The image generation unit 14 generates an image V1A by transforming the first image V1 according to the transformation function determined by the image deformation amount estimation unit 12.

The display control unit 15 displays the image V1A generated by the image generation unit 14 and the second image V2 in a comparable manner on the display 3. Also, the display control unit 15 displays the obtained first and second images V1 and V2 and/or each image generated during execution of the image processing program of this embodiment on the display 3, as necessary, in response to an input by the user, or the like.

Figure 2:
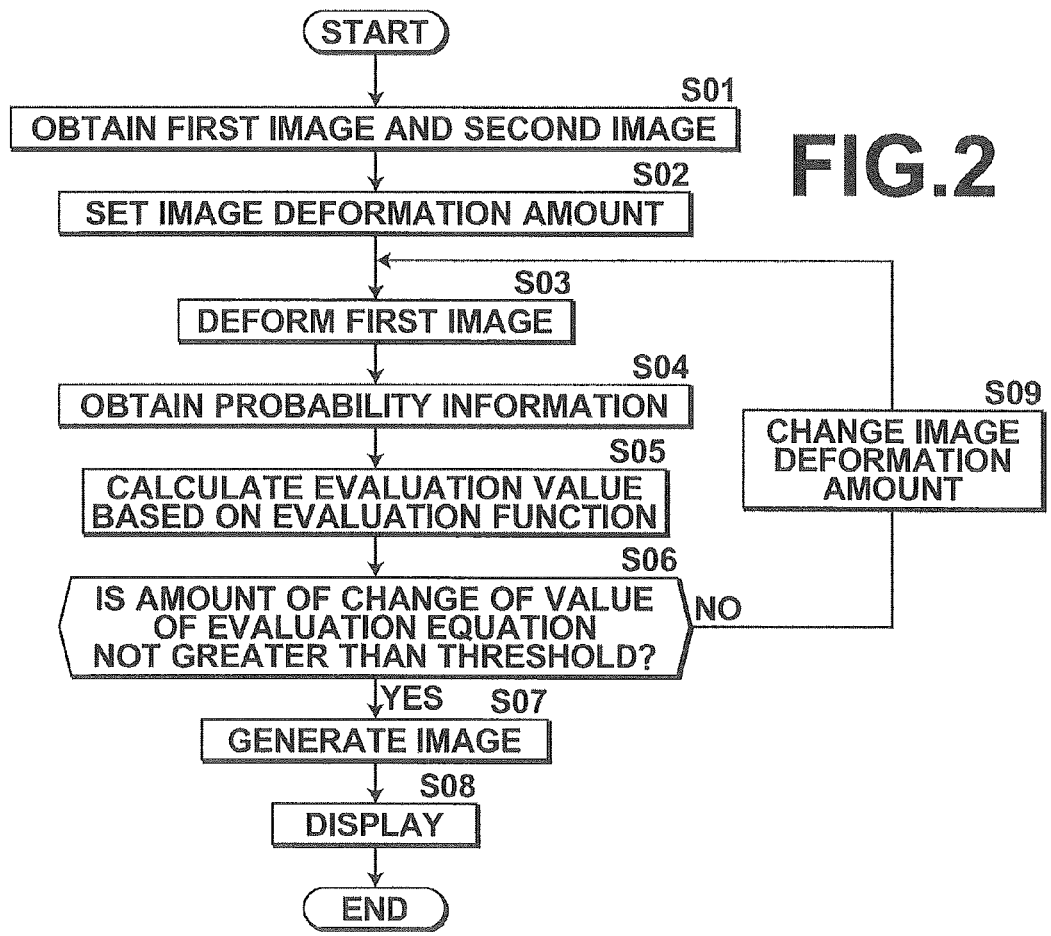
FIG. 2 is a flow chart illustrating operation of the image processing device according to the first embodiment of the invention.

FIG. 2 is a flow chart illustrating a preferred embodiment of the image processing method of the invention. Image processing of this embodiment is described with reference to FIG. 2.

First, the image obtaining unit 11 obtains the first image (first image data) V1 and the second image (second image data) V2 that are obtained by imaging a subject (S01).

Then, the image deformation amount estimation unit 12 sets the image deformation amount μ (S02) and deforms the first image V1 (S03).

Subsequently, the image deformation amount estimation unit 12 obtains pixel values of the deformed first image V1a and the second image V2 and calculates a joint probability distribution function p(f, m;μ) and marginal probability distribution functions p(f) and p(m;μ). Based on the calculated joint probability distribution function p(f, m;μ) and marginal probability distribution functions p(f) and p(m;μ), the probability information obtaining unit 13 obtains the probability information $P_L(m;μ|f)$ by calculating the conditional probability distribution function as described above (S04). Then, the image deformation amount estimation unit 12 calculates, as the evaluation value, an amount of change |S(μ)−S(μ−Δμ)| of the evaluation function S(μ) expressed by Equation (3) (S05). If the calculated amount of change |S(μ)−S(μ−Δμ)| of the evaluation function S(μ) is greater than a predetermined threshold value (N in S06), μ+Δμ, which is obtained by incrementing the image deformation amount μ by a predetermined amount Δμ, is set as a new image deformation amount μ (S09), and the operations in S04 to S05 are repeated. It should be noted that the image deformation amount estimation unit 12 may use, as the evaluation value, an absolute value |∇S(μ)| of a partial derivative of the evaluation function S(μ), in place of the amount of change |S(μ)−S(μ−Δμ)| of the evaluation function S(μ).

Figure 3B:
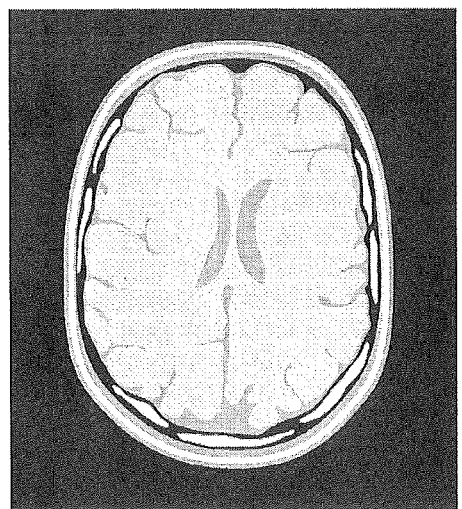
FIG. 3B shows one example of a deformed first image (MR image) and the second image (CT image) after registration.
Figure 3B:
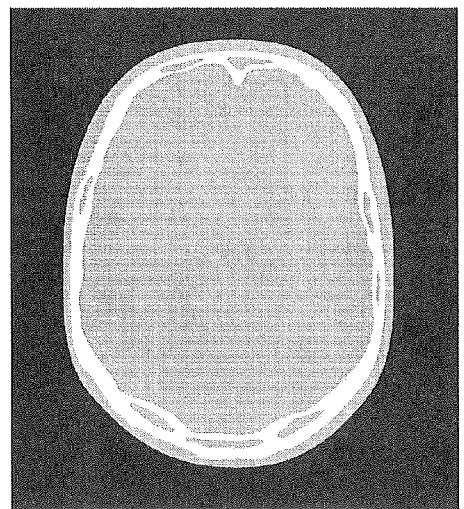

On the other hand, if the calculated amount of change |S(μ)−S(μ−Δμ)|, which is the evaluation value, is not greater than the predetermined threshold value (Y in S06), the image deformation amount estimation unit 12 obtains the image deformation amount μ at this time as the image deformation amount μ that maximizes the evaluation function S(μ), and determines the transformation function for deforming the first image based on this image deformation amount μ. The image generation unit 14 transforms and reconstructs the first image using the determined transformation function to generate the image V1A (S07). Then, the display control unit 15 displays the generated image V1A and the second image V2 side by side in a comparable manner (S08). FIG. 3B shows one example of the generated image V1A and the second image V2 displayed in a comparable manner. In FIG. 3B, the image V1A is registered to the second image V2, where the sizes of the anatomic structures, such as the skull, in the image V1A and the second image V2 conform to each other and the positions of the boundary between the right and left cerebral hemispheres, etc., in the image V1A and the second image V2 conform to each other.

According to the above-described embodiment, the term representing the similarity between pixel values of the deformed first image and the second image in the evaluation function is weighted with the probability information that indicates a probability of a combination of pixel values at each control point of the deformed first image and the control points of the second image. This weighting allows evaluating the similarity as low similarity for an actually impossible combination of pixel values at each control point of the image obtained with the first modality and each control point of the image obtained with the second modality, depending on the probability condition. This allows more accurate evaluation of the similarity than that with the conventional technique, and an image of the first image registered to the second image can preferably be generated as a result.

Further, the term representing the similarity between pixel values of the image obtained with the first modality and the image obtained with the second modality in the evaluation function is weighted with the conditional probability of occurrence of an event where, given an event where each control point of the image obtained with the first modality has a pixel value of f, each corresponding control point of the image obtained with the second modality has a pixel value of m;μ. This allows more accurate calculation of the similarity between the two images depending on the probability of each combination of pixel values of the two images.

Further, in the case where the conditional probability is calculated based on pixel values of the first image and the second image and is used as the probability information, the probability information can be set when there is information of pixel value distributions of the two images. Therefore, it is not necessary to collect or analyze information for setting the probability information, and this facilitates application of the probability information to the evaluation function. Further, in the case where the conditional probability is calculated based on pixel values of the first reference image and the second reference image and is used as the probability information, the probability information can be set when there is information of pixel value distributions of the two images, and this facilitates application of the probability information to the evaluation function. Further, both the amount of mutual information and the conditional probability can be calculated based on the joint probability distribution function p(f, m;μ) and the marginal probability distribution function p(f), and this is computationally efficient.

As a modification of the first embodiment, the probability information may associate, for each subject type, a first range of pixel values obtained by imaging a given type of subject with the first modality with a second range of pixel values obtained by imaging the given type of subject with the second modality, and the evaluation function may be weighted based on the probability information such that the similarity between the deformed first image and the second image is evaluated as low similarity when pixel values of the deformed first image and the second image do not satisfy the first range of pixel values and the second range of pixel values associated with the first range of pixel values. It should be noted that "weighted such that the similarity is evaluated as low similarity" as used herein means being weighted such that a smaller similarity value is calculated in a case where an evaluation function that evaluates that the similarity between the deformed first image and the second image is higher as the similarity is greater is used, or being weighted such that a greater similarity value is calculated in a case where an evaluation function that evaluates that the similarity between the deformed first image and the second image is higher as the similarity is smaller is used.

As one example, the evaluation function in the modification of the first embodiment can be defined as Equation (5) below:

$$p_L(m; \mu \mid f) = \begin{cases} 1, & m^f_{min} \leq m(\mu) \leq m^f_{max} \\ 0, & \text{otherwise} \end{cases} \quad (5)$$

In the following example, for each pixel value f(f∈F) of the image obtained with the second modality, a range $m_{min}^f \leq m(\mu) \leq m_{max}^f$ of pixel values which the image obtained with the first modality may possibly have is stored with being associated with the pixel value f. Then, for each pixel value f (the first range) of the first image, if a pixel value m(μ) of the second image belongs to the associated range $m_{min}^f \leq m(\mu) \leq m_{max}^f$ (the second range), the term representing a measure of correlation between the first image and the second image in the evaluation function is weighted with "1". Otherwise, it is determined that the combination of pixel values is an actually impossible combination of pixel values, and the term representing a measure of correlation between the first image and the second image in the evaluation function is weighted with "0" so that the similarity is evaluated as low similarity.

In the above-described modification of the first embodiment, the corresponding ranges of pixel values of the first image and the second image may be defined according to known information that is obtained by analyzing test images obtained in advance. For example, a range of pixel values shown by each type of subject, such as water, air, each anatomic structure (or each element forming an anatomic structure), etc., in images obtained with the first modality is associated with a range of pixel values shown by each corresponding object, such as water, air, each anatomic structure, etc., in images obtained with the second modality, and the associated ranges are stored as the probability information. Then, the image deformation amount estimation unit 12 may evaluate the similarity as low similarity for a combination of pixel values that does not fall under any of combinations of ranges of pixel values associated as the probability information. In this case, the corresponding ranges of pixel values are set in the probability information based on information of pixel values of two images that are known to show the same subject, and therefore the probability information can be defined more accurately.

Alternatively, the corresponding ranges of pixel values of the first image and the second image may be determined based on theoretical pixel values that are estimated based on the imaging principle of each modality. For example, for each type of object that may possibly be the subject, pixel values in a case where the object is imaged with individual modalities are estimated and stored with being associated with the type of object. For example, for each type of subject, such as water, air, each anatomic structure (or each element forming an anatomic structure), etc., a range of pixel values of an image obtained by imaging the subject with the first modality and a range of pixel values of an image obtained by imaging the subject with the second modality are estimated based on the imaging principles. Then, for each object, the estimated range of pixel values of an image obtained with first modality and the estimated range of pixel values of an image obtained with second modality are stored with being associate with the object. Then, a low weight may be set for the similarity for a combination of pixel values that does not fall under any of combinations of ranges of pixel values associated as the probability information. In this case, the corresponding ranges of pixel values in the probability information are set based on information of pixel values of the two images estimated based on the imaging principles, and therefore the probability information can be defined more accurately.

Further, the probability information in each of the above-described cases may be scaled (normalized) to adjust the weighting. In this case, the weighting can be adjusted such that the weight on the term representing correlation between the first and second reference images is not excessively large (or small), in such a case where the conditional probability becomes a very small value, for example. It should be noted that any of various known methods for adjusting weighting may be applied.

For example, in the case where the conditional probability is used as the probability information, it is preferred to normalize the probability information so that it is less likely to be influenced by the profile of the pixel value distribution. This is because that the value of a probability density function with pixel values being random variables, which is an element used to calculate the conditional probability, fluctuates depending on the profile of the pixel value distribution, such that the value is small when the pixel value distribution is flat and the value is large when the pixel value distribution has a precipitous profile with a concentrated area. Therefore, first, for each pixel value f(f∈F) of the image obtained with the second modality, the range $m_{min}^f \leq m(\mu) \leq m_{max}^f$ of pixel values which the image obtained with the first modality may possibly have is stored with being associated with the pixel value f. Then, for each pixel value f(f∈F) of the image obtained with the second modality, the distribution of pixel values of the first reference image associated with the pixel value f is approximated to a uniform distribution, and a probability density function $P_U(m)$ ($=m_{max}^f-m_{min}^f$) of the first reference image is calculated. Then, the probability information is further weighted with a reciprocal $A_m$ of the probability density function $P_U(m)$ as shown by Equation (6) below:

$$p_L(m; \mu \mid f) = \frac{p_L(f, m; \mu)}{p_L(f) p_U(m)} = A_m \frac{p_L(f, m; \mu)}{p_L(f)} \quad (6)$$

In this case, influence of the distribution profile of the range of pixel values $m_{min}^f < m(\mu) < m_{max}^f$ of the image obtained with the first modality associated with each pixel value f of the image obtained with the second modality can be minimized, and more appropriate weighting which preferably reflects the probability of each combination of pixel values of the image obtained with the first modality and the image obtained with the second modality can be achieved.

Further, although the amount of mutual information expressed by Equation (2) is used as the term representing a measure of correlation between two images obtained by imaging the same subject with different modalities in this first embodiment, an amount of mutual information defined by any of various known methods can be used as the term representing a measure of correlation between two images. Further, other terms, such as a term defining a marginal condition for smoothness of deformation, may also be added to the evaluation function, as long as the term representing a measure of correlation between two images is weighted with the probability information, or any of various known modifications may be made to the evaluation function.

For example, in the first embodiment, the term representing a measure of correlation between two images in the first evaluation function may represent an amount of square loss mutual information in place of the amount of mutual information. In this case, the same effect as that in the above-described first embodiment is obtained. This is because that, in the case where the similarity between the distribution of pixel values of the first image and the distribution of corresponding pixel values of the second image is evaluated using an evaluation function based on the amount of square loss mutual information in the non-rigid registration technique for registering the first image and the second image that are obtained by imaging the same subject with different modalities, the probability of each combination of pixel values obtained depending on the type of each modality, etc., is not evaluated at all and the first problem occurs, similarly to the case where the evaluation function based on the amount of mutual information is used.

The amount of square loss mutual information represents a measure of correlation between the two random variables f and m;μ based on the joint probability distribution function p(f, m;μ) of the two random variables f and m;μ and the marginal probability distribution functions p(f) and p(m;μ) of the two random variables f and m;μ. For example, as the evaluation function for evaluating the correlation between the first image and the second image in the first embodiment, the amount of square loss mutual information may be applied, as shown by Equation (8) below:

$$S(\mu) = \frac{1}{2} \sum_{f \in F} \sum_{m \in M} \left( \frac{p(f, m; \mu)}{p(m; \mu) p(f)} - 1 \right)^2 p(m; \mu) p(f) \quad (8)$$

$$= \frac{1}{2} \sum_{f \in F} \sum_{m \in M} p(f, m; \mu) \frac{p(f, m; \mu)}{p(m; \mu) p(f)} - \frac{1}{2}$$

In Equation (8), f is a discrete probability variable belonging to the set F, and m;μ is a discrete probability variable belonging to the set M. The amount of square loss mutual information is greater as the correlation between the two random variables f and m;μ is higher. In other words, if one of the variables can be estimated with a higher probability when the other variable is given, the amount of information is greater. It should be noted that the amount of square loss mutual information is 0 when the two random variables are completely independent from each other.

In Equation (8), each pixel value m;μ of the deformed image of the image obtained with the first modality and each pixel value f of the image obtained with the second modality are random variables of the amount of square loss mutual information, and the amount of square loss mutual information in Equation (8) indicates the correlation between distributions of the pixel values f of the second image and the pixel values m;μ of the deformed first image. Therefore, the amount of square loss mutual information functions as a measure of similarity between the second image and the deformed first image. It should be noted that the set F is a set of all the pixel values of the deformed first image, and the set M is a set of all the pixel values of the second image.

Further, the present inventor has found that a method where the probability information is introduced in the evaluation function in another aspect (the second aspect) is also effective to address the first problem. Now, this method is described as a second embodiment. In the second embodiment, operations other than an operation to obtain the probability information and an operation to evaluate the similarity between the deformed image V1a of the first image V1 and the second image V2 using the evaluation function S(μ) are the same as those in the first embodiment, and functions of the functional blocks are also the same as those in the first embodiment. In the following description, points that are different from the first embodiment are mainly described, and explanations of the same points as in the first embodiment are omitted.

FIG. 6 is a flow chart illustrating the flow of image processing in the second embodiment. Now, the second embodiment is described according to FIG. 6. First, similarly to the first embodiment, the image obtaining unit 11 obtains the first image (first image data) V1 and the second image (second image data) V2 that are obtained by imaging a subject (S31). Then, similarly to the first embodiment, the image deformation amount estimation unit 12 sets the image deformation amount μ (S32) and deforms the first image V1 (S33). It should be noted that the operations in S31-S33 shown in FIG. 6 correspond to the operations in S01-S03 shown in FIG. 2, respectively.

Subsequently, the probability information obtaining unit 13 obtains pixel values of the deformed first image V1a and the second image V2 and calculates the joint probability distribution function p(f, m;μ) and the marginal probability distribution functions p(f) and p(m;μ). Further, the probability information obtaining unit 13 calculates, as the probability information, a conditional probability of occurrence of an event where each pixel value of a first reference image (a MR image) that is obtained by imaging an additional subject with the first modality (a MR apparatus) are obtained, given an event where each pixel value of a, second reference image (a CT image) that is obtained by imaging the additional subject with the second modality (a CT apparatus) is obtained (S34).

In this embodiment, the probability information obtaining unit 13 prepares, for each of N subjects, a pair of a first reference image obtained by imaging the subject with the first modality and a second reference image obtained by imaging the subject with the second modality (pair of reference images). Then, for each pixel of the first and second reference images of each pair, the probability information obtaining unit 13 associates a pixel value of the pixel of the first reference image with a pixel value of the pixel of the second reference image showing the same subject portion as that shown by the pixel of the first reference image. Then, a conditional probability distribution function $p_L(m;\mu_{ref}|f_{ref})$ is obtained by calculating, based on each pixel value $m;\mu_{ref}$ of the first reference images and pixel values $f_{ref}$ of the second reference images associated with the pixel value $m;\mu_{ref}$ obtained from the N pairs of reference images, a distribution of pixel values $f_{ref}$ of the second reference images for each pixel value $m;\mu_{ref}$ of the first reference images (or for each pixel value of the second reference images), using a known method. It should be noted that the probability information obtaining unit 13 may use any of various known methods as long as the conditional probability distribution function $p_L(m;\mu_{ref}|f_{ref})$ can be calculated. It is assumed here that N pairs of the first reference image and the second reference image that are obtained by imaging the N subjects are used. In order to more accurately calculate the probability information, it is preferable that the number N of the pairs of reference images be greater, and it is preferable that the N subjects be the same type of subjects as that shown in the first image V1 and the second image V2.

Subsequently, the image deformation amount estimation unit 12 applies the thus calculated conditional probability distribution function $p_L(m;\mu_{ref}|f_{ref})$ serving as the probability information $p_L(m;\mu|f)$ to an evaluation function $S_D(\mu)$ expressed by Equation (9) which will be described later, to calculate an amount of change $|S_D(\mu)-S_D(\mu-\Delta\mu)|$ of the evaluation function $S_D(\mu)$ as the evaluation value (S35). It should be noted that, in the operations in S35 and S36, the image deformation amount estimation unit 12 may use an absolute value $|\nabla S_D(\mu)|$ of a partial derivative $S_D(\mu)$ of the evaluation function $S_D(\mu)$, in place of the amount of change $|S_D(\mu)-S_D(\mu-\Delta\mu)|$ of the evaluation function $S_D(\mu)$.

The image deformation amount estimation unit 12 in the second embodiment uses, as a term representing a measure of correlation between a pixel value m;μ of the deformed first image V1a and a pixel value f of the second image V2 (i.e., the term representing a measure of correlation) in the evaluation function $S_D$, a term representing a difference (which may hereinafter be referred to as "difference A") between the joint probability distribution function p(f, m;μ) with a pixel value m;μ of the deformed first image V1a and a pixel value f of the second image V2 being discrete probability variables and the probability information $P_L(m;\mu|f)$. Hereinafter, the evaluation function (which uses, as the term representing a measure of correlation, the evaluation function using the term representing the difference A) may be referred to as "second evaluation function".

In this embodiment, the difference A is defined as a Kullback-Leibler distance (KL distance) between the joint probability distribution function p(f, m;μ) and the probability information $P_L(m;\mu|f)$, as expressed by Equation (9) below:

$$S_D(\mu) = -\sum_{f \in F}\sum_{m \in M} p(f, m; \mu)\log\frac{p(f, m; \mu)}{p_L(m; \mu \mid f)p(f)} \quad (9)$$

In Equation (9), the multiplication between the probability information $P_L(m;\mu|f)$ and the marginal probability distribution function p(f) represents a joint probability distribution (which will hereinafter be referred to as "probability-joint probability distribution") In Equation (9), focusing on the relationship between the joint probability distribution function p(f, m;μ) and the probability-joint probability distribution $P_L(m;\mu|f)*p(f)$, the term representing a measure of correlation represents a difference (difference A) between the joint probability distribution function p(f, m;μ) with a pixel value m;μ of the deformed first image V1a and a pixel value f of the second image V2 being discrete probability variables and the probability-joint probability distribution $P_L(m;\mu|f)*p(f)$. According to Equation (9), a smaller evaluation value is obtained as the joint probability distribution function p(f, m;μ) is nearer to the probability-joint probability distribution $P_L(m;\mu|f)*p(f)$. Therefore, by minimizing the evaluation value of the evaluation function $S_D(\mu)$ the joint probability distribution function of a pixel value m;μ of the deformed first image V1a and a pixel value f of the second image V2 can be approximated to the probability-joint probability distribution $P_L(m;\mu|f)*p(f)$ based on combinations of pixel values of the pairs of reference images.

Therefore, according to Equation (9), a difference between the joint probability distribution function p(f, m;μ) and the probability-joint probability distribution obtained from the pairs of the first reference image and the second reference image is evaluated based on the difference A, and the similarity is evaluated as higher similarity (a lower evaluation value is calculated) for the joint probability distribution function p(f, m;μ) nearer (more similar) to the probability-joint probability distribution based on combinations of pixel values of the pairs of reference images, so that the similarity is evaluated as low similarity (a high evaluation value) is calculated for an actually impossible combination of a pixel value m;μ at each control point of the deformed first image V1a and a pixel value f of the second image V2, based on the probability-joint probability distribution. This allows more accurate evaluation of the similarity than that evaluated with the conventional technique, and an image of the first image V1 that is registered to the second image V2 can preferably be generated, as a result.

By defining the evaluation function as Equation (9), as described above, the similarity can be evaluated low for an actually impossible combination of a pixel value m;μ at each control point of the deformed first image V1a and a pixel value f of the second image V2, and the similarity can be evaluated as higher similarity as the joint probability distribution function of a pixel value m;μ of the deformed first image V1a and a pixel value f of the second image V2 that is nearer to the marginal probability distribution function of the second image V2, based on the above-described difference A.

Subsequently, in the second embodiment, if the amount of change $|S_D(\mu)-S_D(\mu-\Delta\mu)|$ of the evaluation function $S_D(\mu)$ expressed by Equation (9) is greater than a predetermined threshold value (N in S36), the image deformation amount estimation unit 12 sets μ+Δμ, which is obtained by incrementing the image deformation amount μ by a predetermined amount Δμ, as a new image deformation amount μ (S39), and the operations in S34 to S35 are repeated. On the other hand, if the calculated amount of change $|S_D(μ)-S_D(μ-Δμ)|$ of the evaluation function $S_D(μ)$ is not greater than the predetermined threshold value (Y in S36), the image deformation amount estimation unit 12 obtains the image deformation amount μ at this time as the image deformation amount μ that minimizes the evaluation function $S_D(μ)$ and determines the transformation function for deforming the first image based on this image deformation amount μ.

The image generation unit 14 transforms and reconstructs the first image using the determined transformation function to generate the image V1A (S37). Then, the display control unit 15 displays the generated image V1A and the second image V2 side by side in a comparable manner, and the process ends (S38). It should be noted that the operations in S36-S39 shown in FIG. 6 correspond to the operations in S06-S09 shown in FIG. 2, respectively.

It should be noted that, in the second embodiment, the term representing a measure of correlation between a pixel value m;μ of the deformed first image V1a and a pixel value f of the second image V2 in the evaluation function $S_D(μ)$ may be defined by any of various methods, as long as the term can represent a difference between the probability information $P_L(m;μ|f)$ and the joint probability distribution function p(f, m;μ) with a pixel value m;μ of the deformed first image V1a and a pixel value f of the second image V2 being discrete probability variables.

Further, as a third embodiment, an evaluation function that is a combination of the first evaluation function as shown in the first embodiment and the second evaluation function as shown in the second embodiment may be used.

In the third embodiment, operations other than an operation to obtain the probability information and an operation to evaluate the similarity between the deformed image V1a of the first image V1 and the second image V2 using an evaluation function $S_D(μ)-λS_D(μ)$ are the same as those in the first embodiment, and functions of the functional blocks are also the same as those in the first embodiment. In the following description, points that are different from the first embodiment are mainly described, and explanations of the same points as in the first embodiment are omitted.

The evaluation function of the third embodiment is a combination of the second evaluation function $S_D(μ)$ of the second embodiment and the first evaluation function $S(μ)$ (an additional evaluation function).

The first evaluation function in third embodiment corresponds to the first evaluation function in the first embodiment and is defined as the above-described Equation (2). The first evaluation function in the third embodiment evaluates the correlation between distributions of pixel values m;μ of the deformed first image V1a and corresponding pixel values f of the second image V2 to evaluate the similarity between the deformed first image V1a of the first image V1 and the second image V2, and includes a term representing a measure of correlation between a pixel value of the deformed first image and a corresponding pixel value of the second image. For example, the term may represent an amount of mutual information or an amount of square loss mutual information with a pixel value of the deformed first image and a pixel value of the second image being discrete probability variables.

The second evaluation function in the third embodiment corresponds to the second evaluation function in the second embodiment and is defined as the above-described Equation (9). As the probability information $P_L(m;μ|f)$ in Equation (9), the same probability information as in the second embodiment is used. The second evaluation function in the third embodiment evaluates, the similarity between the deformed first image V1a of the first image V1 and the second image V2, the correlation between distributions of pixel values m;μ a of the deformed first image V1a and corresponding pixel values f of the second image V2, and includes a term representing a measure of correlation between a pixel value of the deformed first image and a corresponding pixel value of the second image, and this term represents a difference (difference A) between the joint probability distribution function p(f, m;μ) with a pixel value m;μ of the deformed first image V1a and a pixel value f of the second image V2 being discrete probability variables and the probability information $P_L(m;μ|f)$.

The first evaluation function and the second evaluation function in the third embodiment are introduced in the evaluation function such that the similarity is evaluated as higher similarity when the similarity between the deformed first image and the second image is higher. For example, a weighted sum of the first evaluation function and the second evaluation function can be used as the evaluation function.

In this embodiment, the evaluation function is defined as a weighted sum of the first evaluation function $S(μ)$ and the second evaluation function $S_D(μ)$ as expressed by Equation (10):

$$S(μ)-λS_D(μ) \qquad (10).$$

In Equation (10), λ is a weighting factor that is set as appropriate depending on the condition.

FIG. 7 is a flow chart illustrating the flow of image processing in the third embodiment. Now, the third embodiment is described according to FIG. 7.

First, similarly to the first embodiment, the image obtaining unit 11 obtains the first image (first image data) V1 and the second image (second image data) V2 that are obtained by imaging a subject (S41). Then, similarly to the first embodiment, the image deformation amount estimation unit 12 sets the image deformation amount μ (S42) and deforms the first image V1 (S43). It should be noted that the operations in S41-S43 shown in FIG. 7 correspond to the operations in S01-S03 shown in FIG. 2, respectively.

Subsequently, the image deformation amount estimation unit 12 obtains pixel values of the deformed first image V1a and the second image V2 and calculates the joint probability distribution function p(f, m;μ) and the marginal probability distribution functions p(f) and p(m;μ), and the probability information obtaining unit 13 calculates the conditional probability, similarly to the second embodiment, to obtain the probability information $P_L(m;μ|f)$ (S44).

Then, similarly to the first embodiment, the image deformation amount estimation unit 12 calculates the amount of change $|S(μ)-S(μ-Δμ)|$ of the first evaluation function $S_D(μ)$ expressed by Equation (3) as the evaluation value (S45).

Then, similarly to the second embodiment, the image deformation amount estimation unit 12 calculates the amount of change $|S_D(μ)-S_D(μ-Δμ)|$ of the second evaluation function $S_D(μ)$ expressed by Equation (9) as the evaluation value (S46).

Then, the image deformation amount estimation unit 12 calculates an amount of change of the evaluation equation expressed by Equation (10) as the evaluation value. Namely, based on Equation (10), an amount of change $(\|S(μ)-S(μ-Δμ)|-λ|S_D(μ)-S_D(μ-Δμ)\|)$ of the evaluation equation expressed by Equation (10), which is a weighted sum of the amount of change $|S(\mu)-S(\mu-\Delta\mu)|$ of the first evaluation function and the amount of change $|S_D(\mu)-S_D(\mu-\Delta\mu)|$ of the second evaluation function, is calculated (S47).

It should be noted that, in the operations in S47 and S48, the image deformation amount estimation unit 12 may use a partial derivative $(|\equiv S(\mu)|-\lambda|\nabla S_D(\mu)|)$ of Equation (10) in place of the amount of change $(||S(\mu)-S(\mu-\Delta\mu)|-\lambda|S_D(\mu)-S_D(\mu-\Delta\mu)||)$ of the evaluation value. In this case, the image deformation amount estimation unit 12 calculates, in the operation in S45, an absolute value $|\nabla S(\mu)|$ of a partial derivative $\nabla S(\mu)$ of the first evaluation function $S(\mu)$, in place of the amount of change $|S(\mu)-S(\mu-\Delta\mu)|$ of the first evaluation function $S(\mu)$, and the image deformation amount estimation unit 12 calculates, in the operation in S46, an absolute value $|\nabla S_D(\mu)|$ of a partial derivative $\nabla S_D(\mu)$ of the second evaluation function $S_D(\mu)$, in place of the amount of change $|S_D(\mu)-S_D(\mu-\Delta\mu)|$ of the second evaluation function $\nabla S_D(\mu)$.

Then, if the calculated amount of change $(||S(\mu)-S(\mu-\Delta\mu)|-\lambda|S_D(\mu)-S_D(\mu-\Delta\mu)||)$ of the evaluation function $S(\mu)-\lambda S_D(\mu)$ is greater than a predetermined threshold value (N in S48), $\mu+\Delta\mu$, which is obtained by incrementing the image deformation amount $\mu$ by a predetermined amount $\Delta\mu$, is set as a new image deformation amount $\mu$ (S51), and the operations in S43 to S48 are repeated.

On the other hand, if the calculated amount of change $(|S(\mu)-S(\mu-\Delta\mu)|-\lambda|S_D(\mu)-S_D(\mu-\Delta\mu)||)$ of the evaluation function $S(\mu)-\lambda S_D(\mu)$ is not greater than the predetermined threshold value (Y in S48), the image deformation amount estimation unit 12 obtains the image deformation amount $\mu$ at this time as the image deformation amount $\mu$ that maximizes the evaluation function expressed by Equation (10), and determines the transformation function for deforming the first image based on this image deformation amount $\mu$. The image generation unit 14 transforms and reconstructs the first image using the determined transformation function to generate the image V1A (S49). Then, the display control unit 15 displays the generated image VIA and the second image V2 side by side in a comparable manner, and the process ends (S50). It should be noted that the operations in S48-S51 shown in FIG. 7 correspond to the operations in S06-S09 shown in FIG. 2, respectively.

As a modification of the third embodiment, the term representing a measure of correlation between a pixel value of the deformed first image and a corresponding pixel value of the second image in the first evaluation function may be weighted based on the obtained probability information, as in the first embodiment. For example, the evaluation function shown by Equation (3) may be used in place of $S(\mu)$ in the above-described Equation (10), as shown by Equation (11) below:

$$S_L(\mu)-\lambda S_D(\mu) \qquad (11).$$

In Equation (11), the evaluation function shown by Equation (3) is expressed as $S_L(\mu)$. In Equation (11), $\lambda$ is a weighting factor that is set as appropriate depending on the condition.

In the third embodiment, where the combination of the first evaluation function and the second evaluation function is used, the first evaluation function evaluates the similarity as higher similarity as the correlation between the deformed first image V1a and the second image V2 is higher, and the second evaluation function evaluates the similarity as higher similarity as the difference between the joint probability distribution function $p(f, m;\mu)$ with a pixel value $m;\mu$ of the deformed first image V1a and a pixel value f of the second image V2 being discrete probability variables and the probability information $P_L(m;\mu|f)$, which is estimated from the pairs of the first reference image and the second reference image, is smaller. In this manner, the similarity can be evaluated from the two different points of view to accurately evaluate the correlation between the deformed first image and the second image.

In the case where the first evaluation function is weighted based on the obtained probability information as shown in Equation (11), the advantage of the evaluation function in the first embodiment can further be provided. That is, in the first evaluation function, the term representing the similarity between pixel values of the deformed first image and the second image is weighted with the probability information that indicates a probability of a combination of pixel values at each control point of the deformed first image and the second image. This weighting allows evaluating the similarity as low similarity for an actually impossible combination of a pixel value at each control point of the image obtained with the first modality and a pixel value of the image obtained with the second modality, depending on the probability condition. This allows more preferably generating an image of the first image registered to the second image.

It should be noted that, in place of the first evaluation function in third embodiment, a different evaluation function that can evaluate the correlation between the deformed first image and the second image may be used. Also, the first evaluation function and the second evaluation function may be combined in a different manner as long as the correlation between the deformed first image and the second image can be evaluated.

Next, a fourth embodiment of the invention is described. The fourth embodiment differs from the first embodiment in that the image deformation amount estimation unit 12 divides the deformed first image into a plurality of divided first images according to a predetermined dividing condition and divides the second image into a plurality of divided second image corresponding to the divided first images, and evaluates, for each pair of the divided first image and the corresponding divided second image, the similarity between the deformed first image and the second image based on divided image similarity, which is defined to indicate similarity between distributions of pixel values of the pair of divided images.

In the fourth embodiment, the present inventor focused on a further problem (second problem) that, with respect to the conventional evaluation function for determining the similarity between two images based only on the correlation between distributions of pixel values of two images disclosed in Non-Patent Document 1, as expressed by Equation (2), spatial features of the images cannot be discriminated, which may result in an incorrect determination of the similarity.

For example, with the method disclosed in Non-Patent Document 1, even when the number of subjects and spatial positions of the subjects are different between two images that are obtained by imaging a plurality of subjects belonging to the same range of pixel values, the two images are determined to be similar if the total number of pixels belonging to the same range of pixel values is the same between the two images. Specifically, as to one image that is obtained by imaging the chest of a patient, pixel values of pixels showing the pancreas and the liver belong to the same given range of pixel values. If there the other image that is obtained by imaging the chest of the same patient includes a shadow that has pixel values in the given range of pixel values and the volume of the shadow is the same as the sum of the volumes of the liver and the pancreas in the one image, the two images may possibly be determined to be similar by the method of Non-Patent Document 1.

In view of the second problem, the present inventor has found that it is effective to divide the deformed first image and the second image into regions corresponding to each other according to a predetermined dividing condition to calculate the similarity for each divided region, and evaluate the similarity between the first image and the second image based on the similarity for each divided region. In this case, it is highly likely that a plurality of subjects belonging to the same range of pixel values and located apart from one another are contained in different divided regions. Therefore, such a situation that pixel values showing the plurality of subjects located in different divide regions are evaluated to be correlated with one another is minimized, thereby reducing occurrence of the second problem.

It should be noted that the dividing condition may be any method as long as the deformed first image and the second image can be divided into regions corresponding to each other based on a predetermined rule.

For example, the dividing condition may be defined such that the deformed first image is divided into a plurality of divided first images based on a predetermined first space parameter with respect to a given figure, and the second image is divided into a plurality of divided second images corresponding to the divided first images based on a second space parameter that corresponds to the first space parameter. It should be noted that the "figure" as used herein means a shape that is defined according to a certain rule, and includes a point, a straight line, a plane, a curved line, and a three-dimensional shape, such as a sphere, or a part thereof. Corresponding figures between the first image and the second image may be arbitrarily defined as any of a point, a straight line, a curved line, a plane, a curved surface, a three-dimensional shape, such as a sphere, or a part thereof, etc.; however, it is necessary that positions of the corresponding figures in the first image and the second image correspond to each other, and it is desirable, for the sake of convenience of calculation, that the corresponding figures be the same type of figures. The first and second space parameters are the same type of parameters that are defined according to the same rule with respect to the corresponding figures between the deformed first image V1a and the second image, and each of the first and second space parameters may include one or more parameters. For example, a distance, an angle, etc., may be used as the first and second space parameters.

It should be noted that, in order to render the divided first images and the divided second images to show corresponding ranges, it is necessary to unify the scale between the divided first images and the divided second images. An operation to unify the scale between the divided first images and the divided second images may be performed on the first image and the second image before setting the divided first images and the divided second image of the first and second images, or on the divided first images and the divided second images, based on a pixel spacing and a slice spacing, which are obtained from arbitrary information, such as header information, using a known method.

It should be noted that initial positions of the corresponding figures may be identified by any of known methods. For example, corresponding positions on the first image and the second image may be identified according to positions inputted by the user, or may be identified based on characteristic positions of anatomical structures obtained by a known automatic recognition technique.

The dividing condition in the fourth embodiment prescribes that the deformed first image is divided into a plurality of divided first images depending on the distance from a given position, and the second image is divided into a plurality of divided second images corresponding to the divided first images based on the distance from a position corresponding to the given position on the first image. Then, according to the dividing condition, the evaluation function $S(\mu)$ in the fourth embodiment defines, for each pair of divided images including a divided first image and a corresponding divided second image, the divided image similarity that indicates similarity between distributions of pixel values of the pair of divided images, and evaluates the similarity between the deformed first image V1a and the second image V2 based on each divided image similarity value.

The evaluation function $S(\mu)$ may use any of various methods for calculating the similarity between the deformed first image V1a and the second image V2 based on the divided image similarities. As one example, the evaluation function $S(\mu)$ can be defined by the sum of the plurality of divided image similarity values.

In the fourth embodiment, operations other than the evaluation of the similarity between the deformed first image and the second image using the evaluation function $S(\mu)$ are the same as those in the first embodiment, and functions of the functional blocks are also the same as those in the first embodiment. In the following description, points that are different from the first embodiment are mainly described, and explanations of the same points as in the first embodiment are omitted.

Figure 4A:
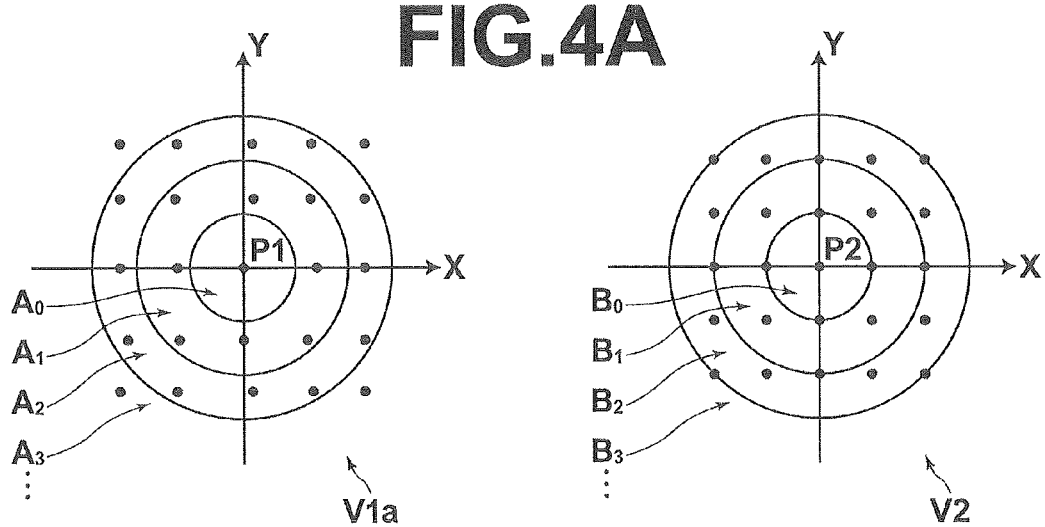
FIG. 4A is a diagram illustrating how a deformed first image and a second image are divided based on the distance from a reference point in a fourth embodiment of the invention.

FIG. 4A is a diagram for explaining how the first and second images are divided in the fourth embodiment. Each of the deformed first image V1a and the second image V2 shown in FIG. 4A shows an x-y plane with the center of a three-dimensional image being the origin. For the purpose of explanation, control points X of the deformed first image V1a are displaced only in the x-y plane. As shown in FIG. 4A, the dividing condition in this embodiment prescribes that reference points P1 and P2 on the deformed first image V1a and the second image V2, respectively, are set, and each of the first image V1a and the second image V2 are divided depending on the distance from the reference point 21, P2. Specifically, each of the deformed first image V1a and the second image V2 is divided into k spherical or hollow spherical regions satisfying $0 \leq d < d_0$, $d_0 \leq d < d_1$, $d_1 \leq d < d_2$, ... and $d_{k-1} \leq d < d_k$ depending on the distance from the reference point. Then, the evaluation function $S(\mu)$ is defined by the sum of divided image similarity values of pairs $(A_0, B_0)$, $(A_1, B_1)$, ... and $(A_k, B_k)$ of the divided first image and the divided second image.

As the evaluation function, Equation (7) below is used:

$$S(\mu) = -\sum_{d \in D}\sum_{f \in F}\sum_{m \in M} p_L(m; \mu \mid f) p(d, f, m; \mu) \log \frac{p(d, f, m; \mu)}{p(d, m; \mu) p(d, f)} \quad (7)$$

In Equation (7), d means each range of distance, and the set D represents a set of ranges of distance $d_0, d_1, d_2, \ldots$ and $d_k$ (k is a positive integer) from a given point on the first image. It should be noted that the range of distance $0 \leq d < d_0$ may be referred to as "range of distance $d_0$". The position of each reference point is inputted by manual operation by the user via the input device 4. Further, in the evaluation function $S(\mu)$ as shown by Equation (7), the similarity (divided image similarity) between the divided first image and the divided second image of each pair $(A_0, B_0)$, $(A_1, B_1)$, ... and $(A_k, B_k)$ is defined by the term of mutual information of each pair of images weighted using the above-described probability information.

FIG. 5 is a flow chart illustrating the flow of operation of the image processing device of the fourth embodiment. The flow of operation is described according to FIG. 5. First, the image obtaining unit 11 obtains the first image (first image data) V1 and the second image (second image data) V2 that are obtained by imaging a subject (S11).

Then, the image deformation amount estimation unit 12 sets the divided second images by dividing the second image according to the dividing condition which is set in advance. Specifically, based on input by the user via the input device, the reference point P2 on the second image V2 is specified, and a distance between the reference point P2 and each control point X of the second image is calculated. Then, depending on the distance from the reference point P2, a plurality of divided second images of the second image V2 are set for given ranges of distance $d_0, d_1, d_2, \ldots$ and $d_k$, and information that identifies each divided image is stored in the memory (S12).

Subsequently, the image deformation amount estimation unit 12 sets the image deformation amount $\mu$ (S13) and deforms the first image V1 using the transformation function g(S14).

Further, the image deformation amount estimation unit 12 sets the divided first images by dividing the first image according to the dividing condition which is set in advance. Specifically, based on input by the user via the input device, the reference point P1 on the deformed first image V1$a$ is specified, and a distance between the reference point P1 and each control point X of the deformed first image V1$a$ is calculated (S15). Then, depending on the distance from the reference point P1, a plurality of divided first images of the deformed first image V1$a$ are set for given ranges of distance $d_0, d_1, d_2, \ldots$ and $d_k$, and information that identifies each divided image is stored in the memory.

Subsequently, the image deformation amount estimation unit 12 obtains pixel values of the deformed first image V1$a$ and the second image V2 and calculates the joint probability distribution function $p(f, m;\mu)$ and the marginal probability distribution functions $p(f)$ and $p(m;\mu)$, and the probability information obtaining unit 13 obtains the probability information $P_L(m;\mu|f)$ by calculating the conditional probability as described above based on the calculated joint probability distribution function $p(f, m;\mu)$ and marginal probability distribution functions $p(f)$ and $p(m;\mu)$ (S16). Then, the image deformation amount estimation unit 12 calculates, as the evaluation value, the amount of change $|S(\mu)-S(\mu-\Delta\mu)|$ of the evaluation function $S(\mu)$ expressed by Equation (7) (S17). If the calculated amount of change $|S(\mu)-(\mu-\Delta\mu)|$ of the evaluation function S is greater than a predetermined threshold value (N in S18), $\mu+\Delta\mu$, which is obtained by incrementing the image deformation amount $\mu$ by a predetermined amount $\Delta\mu$, is set as a new image deformation amount $\mu$ (S21), and the operations in S13 to S18 are repeated. It should be noted that the image deformation amount estimation unit 12 may use, as the evaluation value, an absolute value $|\nabla S(\mu)|$ of a partial derivative of the evaluation function $S(\mu)$ expressed by Equation (7), in place of the amount of change $|S(\mu)-S(\mu-\Delta\mu)|$ of the evaluation function $S(\mu)$.

On the other hand, if the amount of change $|S(\mu)-S(\mu-\Delta\mu)|$ of the evaluation function $S(\mu)$ is not greater than the predetermined threshold value (Y in S18), the image deformation amount estimation unit 12 obtains the image deformation amount $\mu$ at this time as the image deformation amount $\mu$ that maximizes the evaluation function $S(\mu)$, and determines the transformation function for deforming the first image based on this image deformation amount $\mu$. The image generation unit 14 transforms and reconstructs the first image using the determined transformation function to generate the image V1A (S19). Then, the display control unit 15 displays the generated image V1A and the second image V2 side by side in a comparable manner (S20).

According to the fourth embodiment, each of the deformed first image V1$a$ and the second image V2 is divided into a plurality of divided images corresponding to each other, and the evaluation function $S(\mu)$ evaluates the similarity based on the divided image similarity values, each defining the correlation between distributions of pixel values of the divided first and second images for each pair of the divided first image and the divided second image. This minimizes such a situation that pixel values showing a plurality of subjects located in different divided regions are evaluated to be correlated is minimized, thereby reducing occurrence of the second problem. As a result, more accurate evaluation of the similarity can be achieved, and a transformed image of the first image registered to the second image can more preferably be generated.

Further, in the case where the dividing condition prescribes that the deformed first image and the second image are divided according to one space parameter, the distance from the reference point, and the information that identifies the divided first image and the divided second image corresponding to each other for each range of distance $d_0, d_1, d_2, \ldots$ and $d_k$ depending on the distance from the reference point P1, P2 is stored in the memory, computational load for calculating the similarity between the deformed first image and the second image is not increased more than necessary. Further, since the first space parameter is the distance from the reference point, it is easy to set reference figures on the first image and the second image.

As a further modification of the dividing condition in the fourth embodiment, the deformed first image V1$a$ and the second image V2 may be divided depending on angle, in place of the distance. The dividing condition may be such that the deformed first image V1$a$ and the second image V2 are divided for each given range of angle depending on an angle $\theta$ relative to a reference figure. It should be noted that, in this case, an evaluation function obtained by substituting the distance d in Equation (7) with the angle $\theta$ can be used.

Figure 4B:
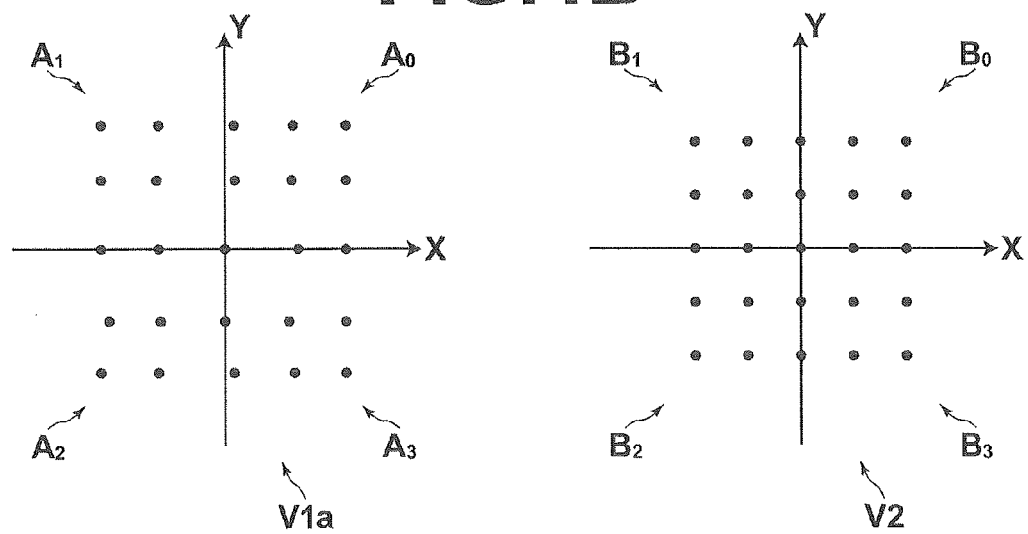
FIG. 4B is a diagram illustrating how a deformed first image and a second image are divided based on an angle from the x-axis in the x-y plane in the fourth embodiment of the invention.

FIG. 4B shows, as another example of the method for dividing the first and second images in the fourth embodiment, an example where the deformed first image V1$a$ and the second image V2 are divided based on the angle $\theta$ from the x-axis (a given axis) in the x-y plane (in a given plane). Each the deformed first image V1$a$ and the second image V2 shown in FIG. 4B shows the x-y plane that passes through the origin of a three-dimensional image. For the purpose of explanation, control points X of the deformed first image V1$a$ are displaced only in the x-y plane. It should be noted that the angle $\theta$ can be obtained as the angle $\theta$ in a case where each of the two images V1$a$ and V2 is represented in a cylindrical coordinate system.

In FIG. 4B, the deformed first image V1$a$ is divided depending on the angle into divided first images $A_0, A_1, A_2$ and $A_3$ of four ranges including $0 \leq \theta < 90°$, $90° \leq \theta < 180°$, $180° \leq \theta < 270°$ and $270° \leq \theta < 360°$ and the second image V2 is divided depending on the angle into divided second images $B_0, B_1, B_2$ and $B_3$ of the four ranges. The range of $\theta$ may be arbitrarily set and the dividing condition may be such that each of the deformed first image V1$a$ and the second image V2 is divided into k ranges including $0 \leq \theta < \theta_0$, $\theta_0 \leq \theta < \theta_1$, $\theta_1 \leq \theta < \theta_2, \ldots$ and $\theta_{k-1} \leq \theta < \theta_k$ depending on the arbitrary angle $\theta$ relative to the reference figure.

As described above, in the case where the dividing condition prescribes that the deformed first image and the second image are divided according to one space parameter, the angle from the reference figure, and the information that identifies the divided first image and the divided second image corresponding to each other for each range of angle $\theta_0, \theta_1, \theta_2, \ldots$ and $\theta_k$ depending on the angle from the reference figure (reference x-axis) is stored in the memory, computational load for calculating the similarity between the deformed first image and the second image is not increased more than necessary.

Alternatively, each of the deformed first image V1a and the second image V2 may be divided based on an arbitrary angle ($0 \leq \theta < \theta_0, \theta_0 \leq \theta < \theta_1, \theta_1 \leq \theta < \theta_2, \ldots$ and $\theta_{k-1} \leq \theta < \theta_k$) relative to the x-axis, and the divided images may be further divides based on an arbitrary angle ($0 \leq \beta < \beta_0, \beta_0 \leq \beta < \beta_1, \beta_1 \leq \beta < \beta_2, \ldots$ and $\beta_{m-1} \leq \beta < \beta_m$) (m is an integer of 0 or more) relative to the z-axis. In this manner, in the case where the deformed first image V1a and the second image V2 are divided based on the angles relative to the two axes, respectively, the deformed first image V1a and the second image V2 can be divided into local three-dimensional regions. This allows more preferably minimizes the first problem, thereby allowing accurate evaluation of the similarity between the deformed first image and the second image.

Still alternatively, the deformed first image V1a may be divided based on distance and may further be divided based on angle to set the divided first images.

Although the divided image similarity for each pair of the divided first image and the corresponding divided second image is calculated according to the evaluation function expressed by Equation (3) in the above-described fourth embodiment, this is not intended to limit the invention. The divided image similarity for each pair of the divided first image and the corresponding divided second image may be calculated according to the second evaluation function in the second embodiment, or according to the evaluation function in the third embodiment, which is a combination of the first evaluation function and the second evaluation function, or any of various evaluation functions that can calculate the similarity between the divided first image and the corresponding divided second image of each pair.

The above-described embodiments are only examples and all the descriptions thereof should not be construed to limit the technical scope of the invention.

Further, various modifications that are made to system configurations, hardware configurations, flows of operations, modular configurations, user interfaces and specific contents of operations in the above-described embodiments without departing from the spirit of the invention are within the technical scope of the invention.

Still further, the functions as the means of the image processing device 1 may be shared by a plurality of computers. Further, any known devices may be used as devices, such as the input device, the display, etc., forming the system.

What is claimed is:

1. An image processing device comprising:
   an image obtaining unit for obtaining a first image obtained by imaging a subject with a first modality and a second image obtained by imaging the subject with a second modality, the second modality being different from the modality with which the first image is obtained;
   an image deformation amount estimation unit for estimating an image deformation amount for deforming the first image to provide a deformed first image that is similar to the second image by deforming the first image and evaluating similarity between the deformed first image and the second image with an evaluation function, the evaluation function evaluating correlation between distributions of pixel values of the deformed first image and corresponding pixel values of the second image; and
   an image generation unit for generating a deformed image of the first image based on the estimated image deformation amount,
   wherein the image deformation amount estimation unit comprises a probability information obtaining unit for obtaining probability information indicating a probability of each combination of corresponding pixel values of the first image and the second image, and
   the evaluation function includes a term representing a measure of correlation between a pixel value of the deformed first image and a corresponding pixel value of the second image, wherein the term evaluates the correlation based on the obtained probability information.

2. The image processing device as claimed in claim 1, wherein the term representing a measure of correlation in the evaluation function is weighted with the probability information.

3. The image processing device as claimed in claim 2, wherein the probability information indicates a conditional probability of occurrence of an event where each pixel value of a first reference image obtained by imaging an additional subject with the first modality is obtained, given an event where each pixel value of a second reference image obtained by imaging the additional subject with the second modality is obtained.

4. The image processing device as claimed in claim 3, wherein the probability information is further weighted with a reciprocal of a probability density function obtained by approximating a pixel value distribution of the first reference image to a uniform distribution in order to adjust the weighting with the conditional probability.

5. The image processing device as claimed in claim 2, wherein the probability information associates, for each type of subject, a first range of pixel values obtained by imaging a given type of subject with the first modality with a second range of pixel values obtained by imaging the given type of subject with the second modality, and
   the evaluation function is weighted based on the probability information such that, if pixel values of the deformed first image and the second image do not satisfy the first range of pixel values and the second range of pixel values associated with the first range of pixel values, the similarity between the deformed first image and the second image is evaluated as being low.

6. The image processing device as claimed in claim 5, wherein the first and second ranges of pixel values are calculated by estimating, for each type of subject, the first and second ranges of pixel values based on imaging principle of the first and second modalities.

7. The image processing device as claimed in claim 2, wherein the term representing a measure of correlation in the evaluation function represents an amount of mutual information or an amount of square loss mutual information with a pixel value of the deformed first image and a pixel value of the second image being discrete probability variables.

8. The image processing device as claimed in claim 1, wherein the probability information represents a conditional probability of occurrence of an event where each pixel value of a first reference image obtained by imaging an additional subject with the first modality is obtained, given an event where each pixel value of a second reference image obtained by imaging the additional subject with the second modality is obtained, and
   the term representing a measure of correlation in the evaluation function represents a difference between the probability information and a joint probability distribution with a pixel value of the deformed first image and a pixel value of the second image being discrete probability variables.

9. The image processing device as claimed in claim 8, wherein the evaluation function is defined by Equation (9) below:

$$S_D(\mu) = -\sum_{f \in F} \sum_{m \in M} p(f, m; \mu) \log \frac{p(f, m; \mu)}{p_L(m; \mu \mid f) p(f)} \quad (9)$$

where f is a pixel value of the second image, m is a pixel value of the first image, F is a set of all pixel values of the second image, M is a set of all pixel values of the first image, m;μ is a pixel value of the deformed first image when the deformation amount of the first image is μ, p(f, m;μ) is a joint probability distribution with the pixel value of the deformed first image and the pixel value of the second image being discrete probability variables, p(f) is a marginal probability distribution with the pixel value of the second image being a discrete probability variable, and $P_L(m;\mu|f)$ is the probability information.

10. The image processing device as claimed in claim 8, wherein the evaluation function includes an additional evaluation function for evaluating correlation between distributions of pixel values of the deformed first image and corresponding pixel values of the second image to evaluate the similarity between the deformed first image obtained by deforming the first image and the second image, and the additional evaluation function includes a term representing a measure of correlation between a pixel value of the deformed first image and a corresponding pixel value of the second image, wherein the term represents an amount of mutual information or an amount of square loss mutual information with the pixel value of the deformed first image and the pixel value of the second image being discrete probability variables.

11. The image processing device as claimed in claim 10, wherein the term representing a measure of correlation between a pixel value of the deformed first image and a corresponding pixel value of the second image in the additional evaluation function is weighted based on the obtained probability information.

12. An image processing method executed on an image processing device, the method comprising the steps of:

obtaining a first image obtained by imaging a subject with a first modality and a second image obtained by imaging the subject with a second modality, the second modality being different from the modality with which the first image is obtained;

estimating an image deformation amount for deforming the first image to provide a deformed first image that is similar to the second image by deforming the first image and evaluating similarity between the deformed first image and the second image with an evaluation function, the evaluation function evaluating correlation between distributions of pixel values of the deformed first image and corresponding pixel values of the second image; and generating a deformed image of the first image based on the estimated image deformation amount, wherein the step of estimating the image deformation amount comprises the step of obtaining probability information indicating a probability of each combination of corresponding pixel values of the first image and the second image, and the evaluation function includes a term representing a measure of correlation between a pixel value of the deformed first image and a corresponding pixel value of the second image, wherein the term evaluates the correlation based on the obtained probability information.

13. A non-transitory computer-readable storage medium storing an image processing program for causing a computer to execute the steps of:

obtaining a first image obtained by imaging a subject with a first modality and a second image obtained by imaging the subject with a second modality, the second modality being different from the modality with which the first image is obtained;

estimating an image deformation amount for deforming the first image to provide a deformed first image that is similar to the second image by deforming the first image and evaluating similarity between the deformed first image and the second image with an evaluation function, the evaluation function evaluating correlation between distributions of pixel values of the deformed first image and corresponding pixel values of the second image; and generating a deformed image of the first image based on the estimated image deformation amount, wherein the step of estimating the image deformation amount comprises the step of obtaining probability information indicating a probability of each combination of corresponding pixel values of the first image and the second image, and the evaluation function includes a term representing a measure of correlation between a pixel value of the deformed first image and a corresponding pixel value of the second image, wherein the term evaluates the correlation based on the obtained probability information.

* * * * *